(12) United States Patent
Chavarria et al.

(10) Patent No.: US 8,591,391 B2
(45) Date of Patent: Nov. 26, 2013

(54) METHOD AND APPARATUS FOR SEPARATING A MATERIAL

(75) Inventors: Jason Chavarria, Warsaw, IN (US); Michael D. Leach, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 875 days.

(21) Appl. No.: 12/758,127

(22) Filed: Apr. 12, 2010

(65) Prior Publication Data

US 2011/0251041 A1 Oct. 13, 2011

(51) Int. Cl.
*B04B 1/04* (2006.01)

(52) U.S. Cl.
USPC ....... 494/4; 494/2; 494/16; 210/516; 210/518

(58) Field of Classification Search
USPC ........ 494/1–4, 16–18, 36; 210/516, 518, 782, 210/789
See application file for complete search history.

(56) References Cited

U.S. PATENT DOCUMENTS

| | | |
|---|---|---|
| 280,820 A | 7/1883 | Hickson et al. |
| 593,333 A | 11/1897 | Park |
| 1,468,313 A | 9/1923 | Lux |
| 1,593,814 A | 7/1926 | Vogel |
| 2,722,257 A | 11/1955 | Lockhart |
| 3,013,557 A | 12/1961 | Pallotta |
| 3,159,159 A | 12/1964 | Cohen |
| 3,409,165 A | 11/1968 | Creith |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,545,671 A | 12/1970 | Ross |
| 3,583,627 A | 6/1971 | Wilson |
| 3,596,652 A | 8/1971 | Winkelman |

(Continued)

FOREIGN PATENT DOCUMENTS

| | | |
|---|---|---|
| AU | 696278 | 1/1999 |
| BR | 9103724 | 3/1993 |

(Continued)

OTHER PUBLICATIONS

"Caps for Corning® and Costar® Plastic Labware," Technical Bulletin. (Dec. 2008) Corning, Incorporated.

(Continued)

*Primary Examiner* — Walter D Griffin
*Assistant Examiner* — Timothy Cleveland
(74) *Attorney, Agent, or Firm* — Harness, Dickey

(57) ABSTRACT

A separation system for separating a multiple component material into at least two fractions. The separation system includes a separation device having a first end, a second end opposite to the first end, and a sidewall that extends between the first end and the second end to define a separation chamber having an interior volume. The system also includes a valve moveable between an open position and a closed position, the valve is mounted at a fixed location within the separation chamber at a position that is closer to the second end than to the first end and is spaced apart from the second end, the valve is operable to isolate a first fraction of the multiple component material having a first density on a first side of the valve from a second fraction having a second density on a second side of the valve that is opposite to the first side.

18 Claims, 11 Drawing Sheets

(56) References Cited

U.S. PATENT DOCUMENTS

| | | |
|---|---|---|
| 3,654,925 A | 4/1972 | Holderith |
| 3,706,305 A | 12/1972 | Berger et al. |
| 3,706,306 A | 12/1972 | Berger et al. |
| 3,723,244 A | 3/1973 | Breillatt, Jr. |
| 3,779,383 A | 12/1973 | Ayres |
| 3,785,549 A | 1/1974 | Latham, Jr. |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,066,549 A | 1/1978 | Oeser et al. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies et al. |
| 4,159,896 A | 7/1979 | Levine et al. |
| 4,187,979 A | 2/1980 | Cullis et al. |
| 4,203,840 A | 5/1980 | Stoeppler et al. |
| 4,204,537 A | 5/1980 | Latham, Jr. |
| 4,225,580 A | 9/1980 | Rothman et al. |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,362,567 A | 12/1982 | Schwarz et al. |
| 4,364,832 A | 12/1982 | Ballies et al. |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al. |
| 4,443,345 A | 4/1984 | Wells |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,735,616 A | 4/1988 | Eibl et al. |
| 4,735,726 A | 4/1988 | Duggins |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,844,818 A | 7/1989 | Smith |
| 4,846,835 A | 7/1989 | Grande |
| 4,850,952 A | 7/1989 | Figdor et al. |
| 4,853,137 A | 8/1989 | Ersson et al. |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,902,281 A | 2/1990 | Avoy |
| 4,909,251 A | 3/1990 | Seelich et al. |
| 4,915,847 A | 4/1990 | Dillon et al. |
| 4,917,801 A | 4/1990 | Luderer et al. |
| 4,928,603 A | 5/1990 | Rose et al. |
| 4,929,242 A | 5/1990 | Desecki et al. |
| 4,939,081 A | 7/1990 | Figdor et al. |
| 4,943,273 A | 7/1990 | Pages et al. |
| 4,946,601 A | 8/1990 | Fiehler |
| 4,957,637 A | 9/1990 | Cornell |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,039,401 A | 8/1991 | Columbus et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker et al. |
| 5,207,638 A | 5/1993 | Choksi et al. |
| 5,217,426 A | 6/1993 | Bacehowski et al. |

(56) References Cited

U.S. PATENT DOCUMENTS

| | | |
|---|---|---|
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,486,359 A | 1/1996 | Caplan et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas et al. |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,795,489 A | 8/1998 | Holm |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,860,937 A | 1/1999 | Cohen |
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,899,874 A | 5/1999 | Jonsson et al. |
| 5,900,245 A | 5/1999 | Sawhney et al. |
| 5,906,934 A | 5/1999 | Grande et al. |
| 5,916,557 A | 6/1999 | Berlowitz-Tarrant et al. |
| 5,916,743 A | 6/1999 | Lake et al. |
| 5,918,622 A | 7/1999 | Perez et al. |
| 5,924,972 A | 7/1999 | Turvaville et al. |
| 5,934,803 A | 8/1999 | Hutter |
| 5,938,621 A | 8/1999 | Kelly et al. |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,980,734 A | 11/1999 | Itoh et al. |
| 5,985,315 A | 11/1999 | Patat et al. |
| 6,007,811 A | 12/1999 | Sawyer et al. |
| 6,010,627 A | 1/2000 | Hood, III |
| 6,020,196 A | 2/2000 | Hu et al. |
| 6,022,306 A | 2/2000 | Dumont et al. |
| 6,025,201 A | 2/2000 | Zelmanovic et al. |
| 6,027,655 A | 2/2000 | Holm |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,117,425 A | 9/2000 | MacPhee et al. |
| 6,123,655 A | 9/2000 | Fell et al. |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |

(56) References Cited

U.S. PATENT DOCUMENTS

| | | |
|---|---|---|
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | DiCesare et al. |
| 6,410,344 B1 | 6/2002 | Chung et al. |
| 6,417,004 B1 | 7/2002 | Brady et al. |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B1 | 10/2002 | Coelho et al. |
| 6,508,778 B1 | 1/2003 | Verkaart et al. |
| 6,516,953 B1 | 2/2003 | DiCesare et al. |
| 6,523,698 B1 | 2/2003 | Dennehey et al. |
| 6,544,162 B1 | 4/2003 | Van Wie et al. |
| 6,544,727 B1 | 4/2003 | Hei |
| 6,558,341 B1 | 5/2003 | Swisher |
| 6,596,180 B2 | 7/2003 | Baugh et al. |
| 6,623,959 B2 | 9/2003 | Harris |
| 6,629,919 B2 | 10/2003 | Egozy et al. |
| 6,638,503 B2 | 10/2003 | Chitte et al. |
| 6,676,629 B2 | 1/2004 | Andrew et al. |
| 6,719,901 B2 | 4/2004 | Dolecek et al. |
| 6,733,471 B1 | 5/2004 | Ericson et al. |
| 6,758,978 B1 | 7/2004 | Bedell |
| 6,777,231 B1 | 8/2004 | Katz et al. |
| 6,803,022 B2 | 10/2004 | DiCesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Wells et al. |
| 7,011,644 B1 | 3/2006 | Andrew et al. |
| 7,077,273 B2 | 7/2006 | Ellsworth et al. |
| 7,077,827 B2 | 7/2006 | Greenfield |
| 7,155,288 B2 | 12/2006 | Soykan et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero et al. |
| 7,354,515 B2 | 4/2008 | Coull et al. |
| 7,374,678 B2 | 5/2008 | Leach et al. |
| 7,411,006 B2 | 8/2008 | Shanbrom |
| 7,470,371 B2 | 12/2008 | Dorian et al. |
| 7,531,355 B2 | 5/2009 | Rodriguez et al. |
| 7,553,413 B2 | 6/2009 | Dorian et al. |
| 7,845,499 B2 | 12/2010 | Higgins et al. |
| 7,914,689 B2 | 3/2011 | Higgins et al. |
| 8,048,321 B2 | 11/2011 | Leach et al. |
| 8,062,534 B2 | 11/2011 | Higgins et al. |
| 2001/0009757 A1 | 7/2001 | Bischof et al. |
| 2002/0035820 A1 | 3/2002 | Farris |
| 2002/0076400 A1 | 6/2002 | Katz et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2002/0192632 A1 | 12/2002 | Hei et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0082152 A1 | 5/2003 | Hedrick et al. |
| 2003/0185803 A1 | 10/2003 | Kadiyala et al. |
| 2003/0191429 A1 | 10/2003 | Andrew et al. |
| 2003/0205538 A1 | 11/2003 | Dorian et al. |
| 2004/0013575 A1 | 1/2004 | Stevens et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0109716 A1 | 5/2005 | Leach et al. |
| 2005/0130301 A1 | 6/2005 | McKay et al. |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0196393 A1 | 9/2005 | Shanbrom |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0051865 A1 | 3/2006 | Higgins et al. |
| 2006/0057693 A1 | 3/2006 | Simon |
| 2006/0083720 A1 | 4/2006 | Fraser et al. |
| 2006/0140923 A1 | 6/2006 | Evangelista et al. |
| 2006/0151384 A1 | 7/2006 | Ellsworth et al. |
| 2006/0175242 A1 | 8/2006 | Dorian et al. |
| 2006/0175244 A1 | 8/2006 | Dorian et al. |
| 2006/0178610 A1 | 8/2006 | Nowakowski |
| 2006/0196885 A1 | 9/2006 | Leach et al. |
| 2006/0243676 A1 | 11/2006 | Swift et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0208321 A1 | 9/2007 | Leach et al. |
| 2008/0011684 A1 | 1/2008 | Dorian et al. |
| 2008/0164204 A1 | 7/2008 | Hatamian et al. |
| 2008/0173593 A1 | 7/2008 | Coull et al. |
| 2008/0193424 A1 | 8/2008 | McKale et al. |
| 2008/0210645 A1 | 9/2008 | Coull et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2009/0014391 A1 | 1/2009 | Leach et al. |
| 2009/0018313 A1 | 1/2009 | Shanbrom |
| 2009/0101599 A1 | 4/2009 | Dorian et al. |
| 2009/0131827 A1* | 5/2009 | Crocker et al. ................ 604/22 |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2010/0055087 A1 | 3/2010 | Higgins et al. |
| 2010/0140182 A1 | 6/2010 | Chapman et al. |
| 2010/0206798 A1 | 8/2010 | Dorian et al. |
| 2010/0256595 A1 | 10/2010 | Leach et al. |
| 2010/0323870 A1 | 12/2010 | Leach et al. |
| 2010/0324450 A1 | 12/2010 | Leach et al. |
| 2011/0014705 A1 | 1/2011 | Leach et al. |

(56) References Cited

U.S. PATENT DOCUMENTS

| | | |
|---|---|---|
| 2011/0020196 A1 | 1/2011 | Grippi et al. |
| 2011/0021334 A1 | 1/2011 | Leach et al. |
| 2011/0036786 A1 | 2/2011 | Ellsworth |
| 2011/0056893 A1 | 3/2011 | Leach et al. |
| 2011/0065183 A1 | 3/2011 | Dorian et al. |
| 2011/0077596 A1 | 3/2011 | Higgins et al. |
| 2011/0168193 A1 | 7/2011 | Leach et al. |
| 2011/0192804 A1 | 8/2011 | Landrigan et al. |
| 2012/0015796 A1 | 1/2012 | Leach et al. |

FOREIGN PATENT DOCUMENTS

| | | |
|---|---|---|
| CA | 1321138 | 8/1993 |
| CA | 2182862 | 6/1996 |
| CA | 2448415 A1 | 12/2002 |
| CN | 1074709 | 7/1993 |
| DE | 56103 | 10/1860 |
| DE | 1443359 | 11/1968 |
| DE | 4202667 | 5/1993 |
| EP | 090997 | 10/1983 |
| EP | 0102773 | 3/1984 |
| EP | 0109374 | 5/1984 |
| EP | 0142339 | 5/1985 |
| EP | 0244834 A2 | 11/1987 |
| EP | 0253198 | 1/1988 |
| EP | 0295771 | 12/1988 |
| EP | 0417818 | 3/1991 |
| EP | 534178 | 3/1993 |
| EP | 0534178 | 3/1993 |
| EP | 0592242 | 4/1994 |
| EP | 1005910 | 6/2000 |
| EP | 1006360 A2 | 6/2000 |
| EP | 1289618 | 3/2003 |
| EP | 1406492 B1 | 4/2004 |
| EP | 1427279 A1 | 6/2004 |
| EP | 1467746 A2 | 10/2004 |
| EP | 1509326 | 3/2005 |
| EP | 1670315 A2 | 6/2006 |
| EP | 1716901 | 11/2006 |
| GB | 854715 | 11/1960 |
| JP | 60-053845 | 3/1985 |
| JP | 60250014 A | 12/1985 |
| JP | 2036872 | 2/1990 |
| JP | 02071747 | 3/1990 |
| JP | 02129224 | 10/2000 |
| JP | 2004-305439 A | 11/2004 |
| JP | 2005098704 | 4/2005 |
| JP | 2006-305365 A | 11/2006 |
| WO | WO-8400905 | 3/1984 |
| WO | WO-8802259 | 4/1988 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9617871 | 6/1996 |
| WO | WO-9617871 A1 | 6/1996 |
| WO | WO-9848938 A1 | 11/1998 |
| WO | WO-0061256 | 10/2000 |
| WO | WO-0074713 A1 | 12/2000 |
| WO | WO-0103756 | 1/2001 |
| WO | WO-0183068 | 11/2001 |
| WO | WO-0238610 A1 | 5/2002 |
| WO | WO-02060925 A1 | 8/2002 |
| WO | WO-02098566 A2 | 12/2002 |
| WO | WO-03015800 | 2/2003 |
| WO | WO-03024215 A1 | 3/2003 |
| WO | WO-03053362 A2 | 7/2003 |
| WO | WO-03088905 | 10/2003 |
| WO | WO-03092894 | 11/2003 |
| WO | WO-03099412 A1 | 12/2003 |
| WO | WO-2004009207 | 1/2004 |
| WO | WO-2004104553 | 12/2004 |
| WO | WO-2005034843 A2 | 4/2005 |
| WO | WO-2007127834 A2 | 11/2007 |
| WO | WO-2007142908 A1 | 12/2007 |
| WO | WO-2009021257 A1 | 2/2009 |

OTHER PUBLICATIONS

"Centrifuge Tubes" Corning Costar brochure. 1996/1997 Catalog pp. 76-77.
"Clotalyst® Autologous Clotting Factor" brochure. (Aug. 15, 2008) Biomet Biologics.
"Corning® 15 and 50 mL Centrifuge Tubes," Life Sciences. (2005) Corning Incorporated.
"Letter CryoSeal FS System. Vaccines, Blood & Biologics," letter. (Jul. 26, 2007) FDA U.S. Food and Drug Administation. http://www.fda.gov/BiologicsBloodVaccines/BloodBloodProducts/ApprovedProducts/Premarket ApprovalsPMAs/ucm091631.htm (Web accessed Aug. 12, 2011).
"Plasmax® Plasma Concentration System" brochure. (Jun. 15, 2008) Biomet® Biologics.
International Search Report and Written Opinon mailed Aug. 9, 2011 for PCT/US2011/031954 claiming benefit of U.S. Appl. No. 12/758,127, filed Apr. 12, 2010.
"Cell Isolation Techniques, Methods and Materials, Working with Enzymes," (2004) (9 pages) Worthington Biochemical Corp.
"Cell Isolation Theory, Tissue Types," (2004) (5 pages) Worthington Biochemical Corp.
"Clotalyst® Autologous Clotting Factor. Would you like to have an autologous thrombin for rapid clotting and haemostasis?" Brochure. Biomet Biologics (Aug. 15, 2008).
"Cytori Celution Cell Concentrate Device," Exhibit 14, 510(k) Summary, FDA approval K060482 (Sep. 28, 2006).
"Frequently Asked Questions, 1. Kits, 2. Engzymes," (2003) 3 pages Worthington Biochemical Corp.
"MarrowStim™ Concentration Kit Peripheral Arterial Disease (PAD) Study" brochure. Web. Jul. 2, 2009 http://www.biomet.com/patients/clinical_recruitment_padstudy.cfm.
"MarrowStim™ Concentration System," brochure. Biomet Biologics Jun. 15, 2008.
"Prosys PRP Kit," brochure Tozai Holdings, Inc. http://tozaiholdings.en.ec21.com/Prosys_PRP_Kit--5467051_5467061.html Printed from Web Aug. 24, 2011.
"Prosys PRP Kit," Tozai Holdings, Inc. EC21 Global B2B Marketplace http://www.ec21.com/product-details/Prosys-PRP-Kit--5467061.html Web Printed from Web Jul. 18, 2011.
"ThermoGenesis Corp. to Supply Autologous Thrombin Kits to Biomet, Inc.," PR Newslink: http://tinyurl.com/4h3up. (Apr. 5, 2005) http://www.noblood.org/press-releases/2128-thermogenesis-corp-supply-autologous-thrombin-kits-biomet-inc [web accessed Sep. 27, 2011].
"Trypsinizing cells." Bart's Cookbook, Web. Apr. 14, 2010. http://pingu.salk.edu/~sefton/Hyper_protocols/trypsin.html.
Anesthesiology, vol. 81, No. 4, pp. 1074-1077, Oct. 1994, Hiromasa Mitsuhata, M.D., et al., "An Anaphylactic Reaction to Topical Fibrin Glue".
Ann Thorac Surg, vol. 53, pp. 530-531, 1992, Mehmet C. Oz, M.D., et al., "Autologous Fibrin Glue From Intraoperatively Collected Platelet-Rich Plasma".
Ann Thorac Surg, vol. 56, pp. 387-389, 1993, Robert L. Quigley, M.D., et al., "Intraoperative Procurement of Autologous Fibrin Glue".
Badiavas, et al., "Treatment of Chronic Wounds With Bone Marrow-Derived Cells," (Reprinted) Arch Dermatol. 139:510-516 (Apr. 2003).
Bang, N.U., et al., "Plasma Protein Requirements for Human Platelet Aggregation" Ann. N.Y. Acad Sci, 201:280-299 (1972).
Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31:3 (1991): 408-11.
Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular opera-

(56) References Cited

OTHER PUBLICATIONS tions. Development of thrombin and factor V inhibitors," *J Thorac Cardiovasc Surg* 105: 5 (1993): 892-7.

BioCUE™ Platelet Concentration System, Dec. 2010. (2 pages).

Biopolymers, vol. 27, pp. 763-774, 1988, Gerald Marx, "Mechanism of Fibrin Coagulation Based on Selective, Cation-Driven, Protofibral Association".

Boomgaard, et al., "Pooled Platelet Concentrates Prepared by the Platelet-Rich-Plasma Method and Filtered with Three Different Filters and Stored for 8 Days." Vox Sang, vol. 68: 82-89, Feb. 1995.

Brodke, et al., "Bone Grafts Prepared with Selective Cell Retention Technology Heal Canine Segmental Defects as Effectively as Autograft", SCR-Enriched Bone Crafts Heal Canine Segmental Defects, Journal of Orthopaedic Research (May 2006) pp. 857-866.

Casali, B., F. Rodeghiero, A. Tosetto, B. Palmieri, R. Immovilli, C. Ghedini, and P. Rivasi. "Fibrin glue from single-donation autologous plasmapheresis." Transfusion 32:7 (1992): 641-3.

Clotalyst™, Automatic Clotting Factor, Would you like to have an autologous thrombin for rapid clotting and haemostasis?, brochure, Biomet Biologics, Inc., Feb. 2007 (12 pages).

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May 1976).

Connolly, "Injectable Bone Marrow Preparations to Stimulate Osteogenic Repair," Clinical Orthopaedics and Related Research 313:8-18 (Apr. 1995).

Connolly, John, M.D., et al. "Development of an Osteogenic Bone-Marrow Preparation." The Journal of Bone and Joint Surgery, Incorporated. vol. 71-A, No. 5 (Jun. 1989) pp. 684-691.

Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.

De Ugarte, et al., "Comparison of Multi-Lineage Cells from Human Adipose Tissue and Bone Marrow," Cells Tissues Organs 174:101-109 (2003).

De Ugarte, et al., "Differential Expression of Stem Cell Mobilization-Associated Molecules on Multi-Lineage Cells from Adipose Tissue and Bone Marrow," Immunology Letters 89:267-270 (2003).

DelRossi, A. J., A. C. Cernaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100:2 (Aug. 1990): 281-6.

DePalma, L., et al., "The preparation of fibrinogen concentrate for use as fibrin glue by four different methods." Transfusion (1993) vol. 33, No. 9; pp. 717-720.

DeUgarte, M.D., Daniel A., et al., "Future of Fat as Raw Material for Tissue Regeneration," (Feb. 2003) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*, ed. I. Kelman Cohen, Robert F. Diegelmann, and William J. Lindblad. 581-600. 1st ed., vol. Philadelphia: W.B. Saunders Company, 1992).

Eppley, et al., "Platelet Quantification and Growth Factor Analysis from Platelet-Rich Plasma: Implications for Wound Healing," Plastic and Reconstructive Surgery, 114(6):1502-1508 (Nov. 2004).

Epstein, G. H., R. A. Weisman, S. Zwillenberg, and A. D. Schreiber. "A new autologous fibrinogen-based adhesive for otologic surgery." *Ann Otol Rhinol Laryngol* 95 (May 25-26, 1985) 40-5.

Fibrostik™ Plasma Concentrator, Attention Operating Surgeon, Cell Factor Technologies, Inc., Jul. 2003.

First clinical results: Kuderma, H. and Helene Metres. "Die klinische Anwendung der Klebung van Nervenanastomosen mit Gerinnungssubstanzen bei der Rekonstruction verletzter peripherer Nerven." Wein Klin Wochenschr 87 (Aug. 15, 1975): 495-501.

Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Friesen, M.D., Robert, et al. "Blood Conservation During Pediatric Cardiac Surgery: Ultrafiltration of the Extracorporeal Circuit Volume After Cardiopulmonary Bypass." Anesth. Analg 1993: 77-702-7.

Galois, et al., "Cartilage Tissue Engineering: State-of-the-Art and Future Approaches," Pathol Biol (Paris), 53(10), Dec. 2005.

Gibble, J. W. and P. M. Ness. "Fibrin glue: the perfect operative sealant?" *Transfusion* 30 (Aug. 1990): 741-7.

Gimble, Jeffrey M., "Adipose-Derived Stem Cells for Regenerative Medicine," Circulation Research (May 11, 2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (Feb. 29, 2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS® II System, Gravitational Platelet Separation System, "Accelerating the Body's Natural Healing Process," Biomet Biologics (Jul. 15, 2006) 16 pages.

GPS® II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS® II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Grove, et al., "Plasticity of Bone Marrow-Derived Stem Cells," Stem Cells: Concise Review, 22, Jan. 2004.

Guilak, Frank, et al., "Adipose-derived adult stem cells for cartilage tissue engineering," Biorheology 41 (2004) pp. 389-399, IOS Press.

Harris, E.L.V. Concentration of the Extract. In. Protein Purification Methods: A Practical Approach Harris, E.L.V.; Angel, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.

Harvest SmartPrep PRP-20 Procedure Pack, "Instructions for Use" (date unknown).

Harvest Technologies brochure, SmartPrep2 (2002).

Hattori, et al., "Osteogenic Potential of Human Adipose Tissue-Derived Stromal Cells as an Alternative Stem Cell Source," Cells Tissues Organs (2004) 178:2-12 Karger.

Haynesworth, S.E. et al. "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).

Hennis, H. L., W. C. Stewart, and E. K. Jeter. "Infectious disease risks of fibrin glue [letter]." *Ophthalmic Surg* 23 (Sep. 1992): 640.

(56) References Cited

OTHER PUBLICATIONS

Hernigou, et al., "Percutaneous Autologous Bone-Marrow Grafting for Nonunions. Influence of the Number and Concentration of Progenitor Cells," Journal of Bone & Joint Surgery, 87-A(7):1430-1437 (Jul. 2005).
Hom, D., et al. "Promoting Healing with Recombinant Human Platelet-Derived Growth Factor-BB in a Previously Irradiated Problem Wound." The Laryngoscope, vol. 113 (pp. 1566-1671) Sep. 2003.
Hood, Andrew G., et al., "Perioperative Autologous Sequestration III: A New Physiologic Glue with Wound Healing Properties," (Jan. 1993) vol. 14 pp. 126-129.
International Preliminary Examination Report and Written Opinion issued Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085 filed Feb. 27, 2009.
International Preliminary Report on Patentability and Written Opinion mailed Oct. 13, 2011 for PCT/US2010/029957 which claims benefit of U.S. Appl. No. 12/417,789, filed Apr. 3, 2009.
International Preliminary Report on Patentability completed Aug. 13, 2009 for PCT/US2008/004687 claiming benefit of U.S. Appl. No. 60/911,407, filed Apr. 12, 2007.
International Preliminary Report on Patentability mailed Jan. 26, 2012 for PCT/US2010/041942 claiming benefit of U.S. Appl. No. 12/504,413, filed Jul. 16, 2009.
International Search Report and Written Opinion mailed Jul. 2, 2008 for International Application No. PCT/US2008/004687 which claims priority to U.S. Appl. No. 60/911,407, filed Apr. 12, 2007.
International Search Report and Written Opinion mailed Jul. 3, 2009 for PCT/US2009/035564 claiming benefit of U.S. Appl. No. 61/078,178, filed Jul. 3, 2008.
International Search Report and Written Opinion mailed Jul. 30, 2010 for PCT/US2010/029957 which claims benefit of U.S. Appl. No. 12/417,789, filed Apr. 3, 2009.
International Search Report and Written Opinion mailed Nov. 7, 2011 for PCT/US2011/045290 claiming benefit of U.S. Appl. No. 12/846,944, filed Jul. 30, 2010.
International Search Report and Written Opinion mailed Oct. 8, 2010 for PCT/US2010/041942 claiming benefit of U.S. Appl. No. 12/504,413, filed Jul. 16, 2009.
International Search Report for International Application No. PCT/US/0316506 mailed Oct. 13, 2003 which claims benefit of U.S. Appl. No. 60/383,013, filed May 24, 2002.
International Search Report for International Application No. PCT/US2007/012587 mailed Nov. 6, 2007 which claims benefit of U.S. Appl. No. 11/441,276, filed May 25, 2006.
Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).
Jackson, C. M. and Y. Nemerson. "Blood coagulation." *Annu Rev Biochem* 49 (Aug. 11, 1980):765-811).
Jayadev, Suprya. "Trypsinization of Adherent Cells." Aug. 8, 1991. Web. Apr. 14, 2010 http://www.duke.edu/web/ceramide/protocols/0005.html.
Johnstone, et al., "Autologous Mesenchymal Progenitor Cells in Articular Cartilage Repair", Clinical Orthopaedics and Related Research 367S:S156-S162 (Oct. 1999).
Jorgensen, et al., "Stem Cells for Repair of Cartilage and Bone: The Next Challenge in Osteoarthritis and Rheumatoid Arthritis," Annals of Rheumatic Diseases, Aug. 2000.
Journal of Oral Maxillofacial Surgery, vol. 43, pp. 605-611, Helene Matras, M.D., "Fibrin Seal: The State of the Art" (1985).
Karpatkin, S., "Heterogeneity of Human Platelets. VI., Correlation of Platelet Function with Platelet Volume", Blood, vol. 51, No. 2 (Feb. 1978).
Kjaergard, H. K., U. S. Weis-Fogh, H. Sorensen, J. Thiis, and I. Rygg. "A simple method of preparation of autologous fibrin glue by means of ethanol." *Surg Gynecol Obstet* 175 (Jan. 1992): 72-3.
Kjaergard, H. K., Fogh Us Weis, and J. J. ThHs. "Preparation of autologous fibrin glue from pericardial blood." *Ann Thorac Sur* 55 (Feb. 1993): 543-4.
Kumar, Vijay et al. "Stability of Human Thrombin Produced From 11 ml of Plasma Using the Thrombin Processing Device," Journal of American Society of Extra-Corporeal Technology. JECT: Mar. 2005:37; 390-395.
Kumar, Vijay et al. "Whole Blood Thrombin: Development of a Process for Intra-Operative Production of Human Thrombin." Journal of American Society of Extra-Corporeal Technology. JECT: Apr. 2007; 39:18-23.
Kumar, Vijay et al., "Autologous Thrombin: Intraoperative Production From Whole Blood." Journal of American Society of Extra-Corporeal Technology. JECT: Apr. 2008; 40:94-98.
Laryngoscope vol. 99, pp. 974-976, Sep. 1989, Kyosti Laitakari, M.D., et al., "Autologous and Homologous Fibrinogen Sealants: Adhesive Strength".
Laryngoscope, vol. 95, pp. 1074-1076, Sep. 1985, Karl H. Siedentop, M.D., et al., "Autologous Fibrin Tissue Adhesive".
Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".
Lasher, Lisa, M.D., "My Experience with PRP," PowerPoint presentation, http://www.cellfactortech.com/global_products.cfm, printed Sep. 16, 2005.
Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.
Lerner, R. and N. S. Binur. "Current status of surgical adhesives." *J Surg Res* 48 (Feb. 1990): 165-81.
Longas, Maria O., "An Improved Method for the Purification of Human Fibrinogen." J. Biochem (1980) vol. 11, pp. 559-564.
Lu, et al., "Bone Marrow Mesenchymal Stem Cells: Progress in Bone/Cartilage Defect Repair," 19(1), Jan. 2002.
Marrowstim Concentration System, Biomet Biologics, Inc., 20 pages (REV Feb. 15, 2008).
Marx, Gerard, et al., "Heat Denaturation of Fibrinogen to Develop a Biomedical Matrix." Journal of Biomedical Materials Research Part B: Applied Biomaterials (Apr. 2007) pp. 49-57.
Masri, Marwan A., et al. "Isolation of Human Fibrinogen of High Purity and in High Yield Using Polyethylene Glycol 1000." Thromb Haemostas (Stuttgart) (1983) vol. 49 (2); pp. 116-119.
Matras, Helene, H. P. Dinges, H. Lassmann, and B. Mamoli. "Zur nahtlosen interfaszikularen Nerventransplantation im Tierexperiment." Wein Med Woschtr 122:37 (1972): 517-523.
Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).
Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).
Minntech® Filtration Technologies Group, "Renaflo® II Hemofilter," Minntech Corporation (2004); http://www.minntech.com/ftg/products/renaflo/index.html, printed Jul. 15, 2004 (2 pages).
Molnar, Amy, "Stem Cells from Muscles Can Repair Cartilage, Study Finds Genetically Engineered Muscle-Derived Stem Cells Improved Cartilage Repair in Rats", American College of Rheumatology, (2005).
Moretz, W., Jr., J Shea Jr., J. R. Emmett, and J Shea. "A simple autologous fibrinogen glue for otologic surgery." *Otolaryngol Head Neck Surg* 95 (Jul. 1986): 122-4.
Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (Dec. 2005) pp. 2542-2547, American Heart Association, Inc.
Nathan, Suresh,, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.

(56) References Cited

OTHER PUBLICATIONS

Nilsson, et al., "Bone Repair Induced by Bone Morphogenetic Protein in Ulnar Defects in Dogs," The Journal of Bone and Joint Surgery, vol. 68 B., No. 4, Aug. 1986.

Orphardt, Charles E., "Denaturation of Proteins," Virtual Chembook, Elmhurst College (2003) 3 pages. http://www.elmhurst.edu/~chm/vchembook/568denaturation.html (web accessed Mar. 9, 2011).

Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".

Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.

Planat-Bénard, V., et al., "Spontaneous Cardiomyocyte Differentiation From Adipose Tissue Stroma Cells," Adipose-Derived Cell Cardiomyocyte (Feb. 6, 2004) pp. 223-229 American Heart Association, Inc.

Ponticiello, Michael S., "A Rapid Technique for the Isolation and Concentration of Stem Cells from Human Bone Marrow", Cell Factor Technologies, Inc. (2006) 2 pages.

Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.

Rigotti, M.D., et al, "Clinical Treatment of Radiotherapy Tissue Damage by Lipoaspirate Transplant: a Healing Process Mediated by Adipose-Derived Adult Stem Cells," Plastic and Reconstructive Surgery, Breast, PRS Journal vol. 119, No. 5, Stem Cell Therapy for Angiogenesis, (Apr. 15, 2007) pp. 1409-1422.

Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (Apr. 15, 2007) pp. 1423-1424.

Sanal, M. "Does fibrin glue cause foreign body reactions? [letter]." Eur J Pediatr Surg 3 (1992): 190 (1 page).

Sanal, M., H. Dogruyol, A. Gurpinar, and O. Yerci. "Does fibrin glue cause foreign body reactions?" Eu r J Pediatr Surg 2 (1992): 285-6.

Schmidt, K.G., et al., "Labelling of Human and Rabbit Platelets with Indium-Oxine Complex", 23:97-106 (1979).

Schmidt, K.G., et al., "Preparation of Platelet Suspensions from Whole Blood in Buffer", Scand. J. Hoemato, 23:88-96 (1979).

Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (Apr. 10, 2007) pp. 818-827 AlphaMed Press.

Semple, Elizabeth, PhD, et al. "Quality of Thrombin Produced From the Patient's Own Plasma Using the TPD Tradmark in Here, a New Thrombin-Processing Device." Journal of American Society of Extra-Corporeal Technology. JECT: 2005; 37:196-200.

Sierra, D. H. "Fibrin sealant adhesive systems: a review of their chemistry, material properties and clinical applications." J Biomater Appl 7 (Apr. 1993): 309-52.

Sigma-Aldrich® Alkaline Phosphatase (Procedure No. 85), drug fact sheet, (2003) pp. 1-2, Sigma-Aldrich, Inc.

Silver, Frederick H., et al., "Review Preparation and use of fibrin glue in surgery." Biomaterials 16 (1995) pp. 891-903.

Solem, Jan Otto, et al., "Hemoconcentration by Ultrafiltration During Open-Heart Surgery," Scand J Thor Cardiovasc Surg 22:271-274, 1988.

Sutton, Robin G., et al. "Comparison of Three Blood-Processing Techniques During and After Cardiopulmonary Bypass." Ann Thorac Surg (1993) vol. 56; pp. 941-943.

Swift, Mathew J., et al., "Characterization of Growth Factors in Platelet Rich Plasma," 1-Cell Factor Technologies, http://www.cellfactortech.com/global_products.cfm, printed Sep. 16, 2005.

Symphony II Platelet Concentrate System/PCS brochure; "Increasing bone graft bioactivity through reproducible concentrations of natural growth factors," DePuy (Jan. 2003).

Takahashi, Kazutoshi et al., "Induction of Pluripotent Stem Cells from Adult Human Fibroblasts by Defined Factors," Cell, (Nov. 30, 2007) pp. 1-12, Elsevier Inc.

The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".

The Sports Medicine Center, "Knee Cartilage Implantation", Carticel™, "Autologous Cultured Chondrocyte Implantation", http://www.orthoassociates.com/carticel.htm (printed Apr. 6, 2006).

The Stone Clinic, "Platelet Rich Plasma (PRP)", web site printed May 2006.

Weis-Fogh, U. S. "Fibrinogen prepared from small blood samples for autologous use in a tissue adhesive system." Eur Surg Res 20 (1988): 381-9.

Weisman, MD., Robert A., "Biochemical Characterization of Autologous Fibrinogen Adhesive," Laryngoscope 97: Oct. 1987; pp. 1186-1190.

Wiseman, David M., David T. Rovee, and Oscar M. Alverez. "Wound Dressings: Design and Use." In Wound Healing: Biochemical & Clinical Aspects,ed. I. Kelman Cohen, Robert F. Diegelmann, and William J. Lindblad. 562-580. 1st ed., vol. Philadelphia: W. B. Saunders Company, 1992.

Woodell-May, et al., "Producing Accurate Platelet Counts for Platelet Rich Plasma: Validation of a Hematology Analyzer and Preparation Techniques for Counting," Scientific Foundation, Journal of Camiofacial Surgery 16(5):749-756 (Sep. 2005).

Written Opinion of the International Preliminary Examining Authority mailed Mar. 17, 2009 for International Application No. PCT/US2008/004687 which claims priority to U.S. Appl. No. 60/911,407, filed Apr. 12, 2007.

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

\* cited by examiner

METHOD AND APPARATUS FOR SEPARATING A MATERIAL

FIELD

The present disclosure relates to methods and apparatuses for separating biological materials, such as a selected fraction from a multiple component biological material.

BACKGROUND

This section provides background information related to the present disclosure, which is not necessarily prior art.

Various cellular or biological materials can be used to facilitate the healing or recovery process in a human patient. Selected cell types, such as stromal cells, pluripotent or multipotent stem cells, or fully differentiated cells can be applied therapeutically to the patient. For example, stem cells can be applied to an affected area of the patient, such as an area that may be damaged due to injury, chemotherapy, or radiation therapy, to assist in healing the area through differentiation of the stem cells and regeneration of the affected cells.

In performing a therapeutic procedure on a human patient using undifferentiated cells, such as stem cells or stromal cells, the undifferentiated cells can be obtained from various sources, including the patient's own anatomy. Accordingly, certain autologous cells can be applied to or injected into various portions of the patient's anatomy. Generally, a whole tissue, such as adipose tissue, or whole blood sample, can be obtained from the patient during a first procedure, selected cells can be separated from the whole tissue or blood sample, and the selected, separated cells can be reapplied to or injected into the patient during a subsequent procedure.

SUMMARY

This section provides a general summary of the disclosure, and is not a comprehensive disclosure of its full scope or all of its features.

The present teachings provide for a separation system for separating a multiple component material into at least two fractions. The separation system includes a separation device having a first end, a second end opposite to the first end, and a sidewall that extends between the first end and the second end to define a separation chamber having an interior volume. The system also includes a valve moveable between an open position and a closed position, the valve is mounted at a fixed location within the separation chamber at a position that is closer to the second end than to the first end and is spaced apart from the second end, the valve is operable to isolate a first fraction of the multiple component material having a first density on a first side of the valve from a second fraction having a second density on a second side of the valve that is opposite to the first side.

The present teachings further provide for a separation system for separating a multiple component material into at least two fractions that includes a separation device and a valve. The separation device has a first end, a second end opposite to the first end, and a sidewall that extends between the first end and the second end to define a separation chamber having an interior volume. The valve is mounted at a fixed positioned within the separation chamber at a position that is closer to the second end than to the first end and is spaced apart form the second end. The valve includes a screen, a flexible valve actuation member, and a sealing member. The flexible valve actuation member is movable in response to gravitational forces applied to the separation device. The sealing member is supported by the flexible valve actuation member. The flexible valve actuation member and the sealing member extend in a plane perpendicular to a longitudinal axis of the separation chamber and the sealing member contacts the screen to prevent the passage of materials through the screen when the valve is in a closed position. The flexible valve actuation member and the sealing member bend toward the second end when the valve is in an open position in response to gravitational forces exerted upon the separation device such that the sealing member is spaced apart from the screen to permit the passage of material through the screen.

The present teachings also provide for a method for isolating at least two fractions of a multiple component material. The method includes the following: loading the multiple component material into a separation chamber of a separation device between a valve mounted at a fixed position in the separation chamber and a first end of the device, the first end is opposite to a second end and a sidewall extends between the first end and the second end to define the separation chamber having an interior volume; centrifuging the separation device such that the valve moves to an open position in response to gravitational forces exerted on the device to permit a first fraction of the multiple component material of a first density to pass through the valve toward the second end; ceasing centrifugation of the separation device to permit the valve to move to a closed position, thus isolating the first fraction of the first density between the valve and the second end and isolating a second fraction of a second density that is less dense than the first density between the valve and the first end; and withdrawing at least one of the first fraction and the second fraction from the separation chamber for use in a subsequent procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
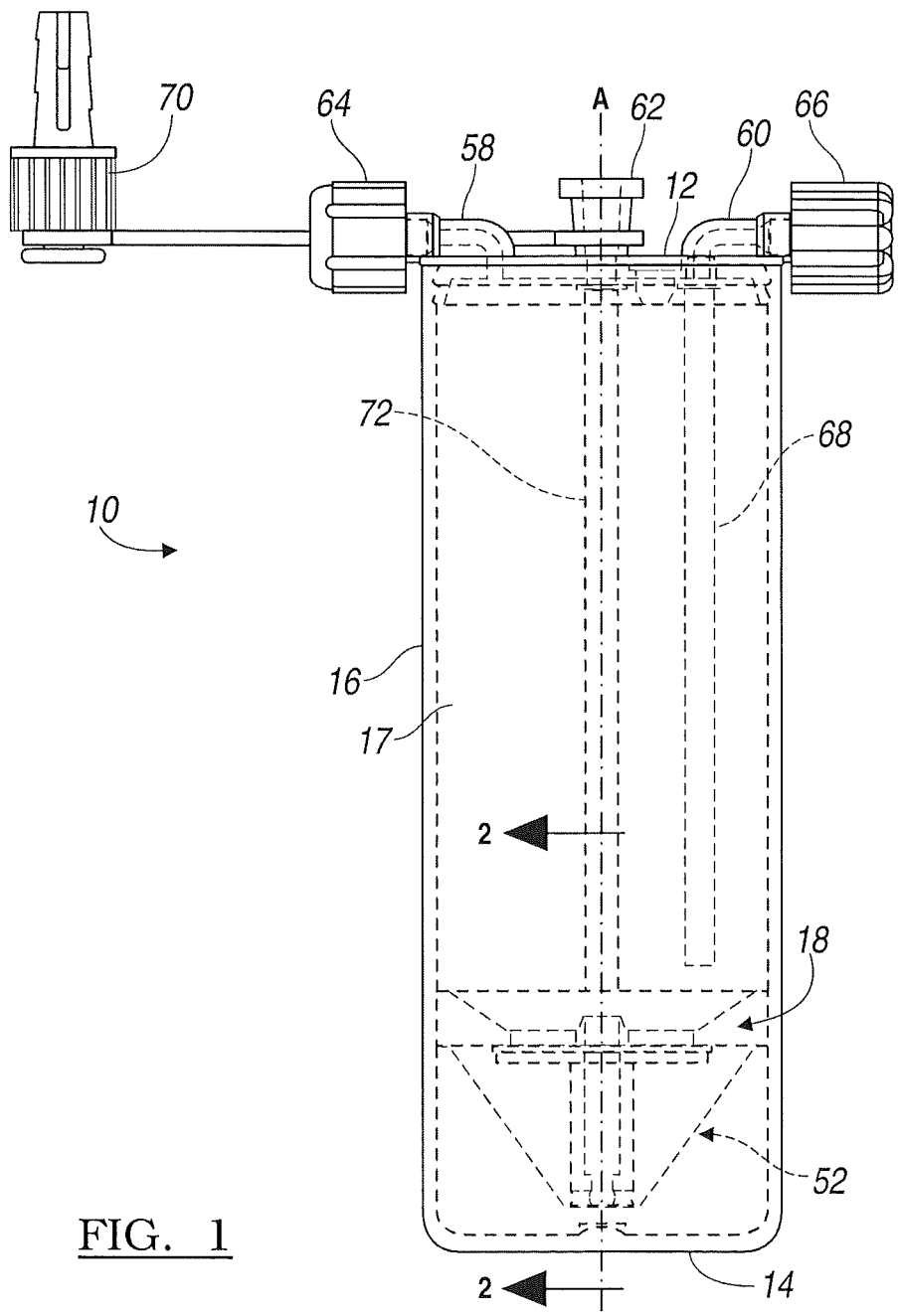
FIG. 1 is a side view of a separation device according to the present teachings.
Figure 2:
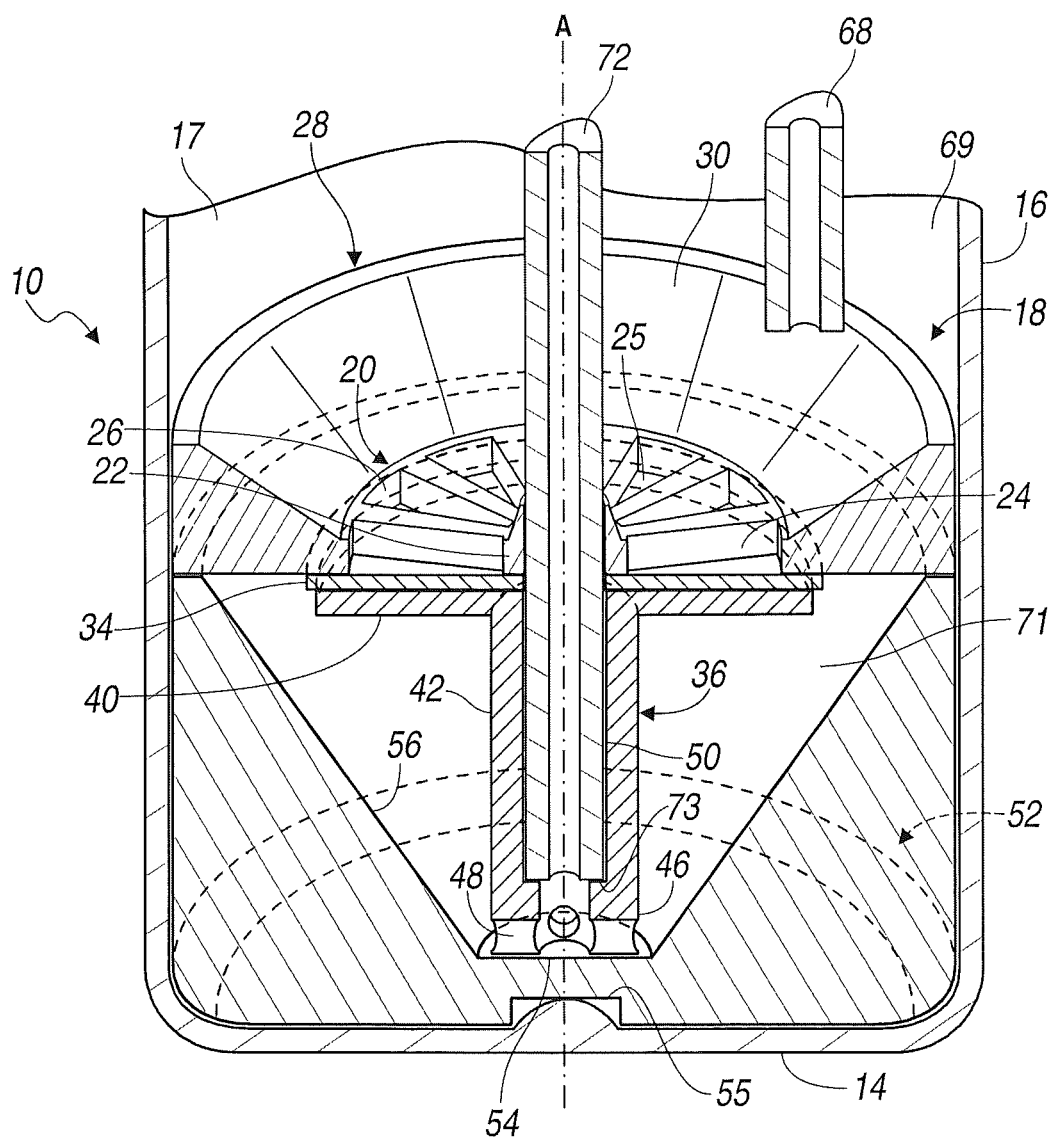
FIG. 2 is a side cross-sectional perspective view taken along line 2-2 of FIG. 1 illustrating a valve according to the present teachings in a closed position.
Figure 3:
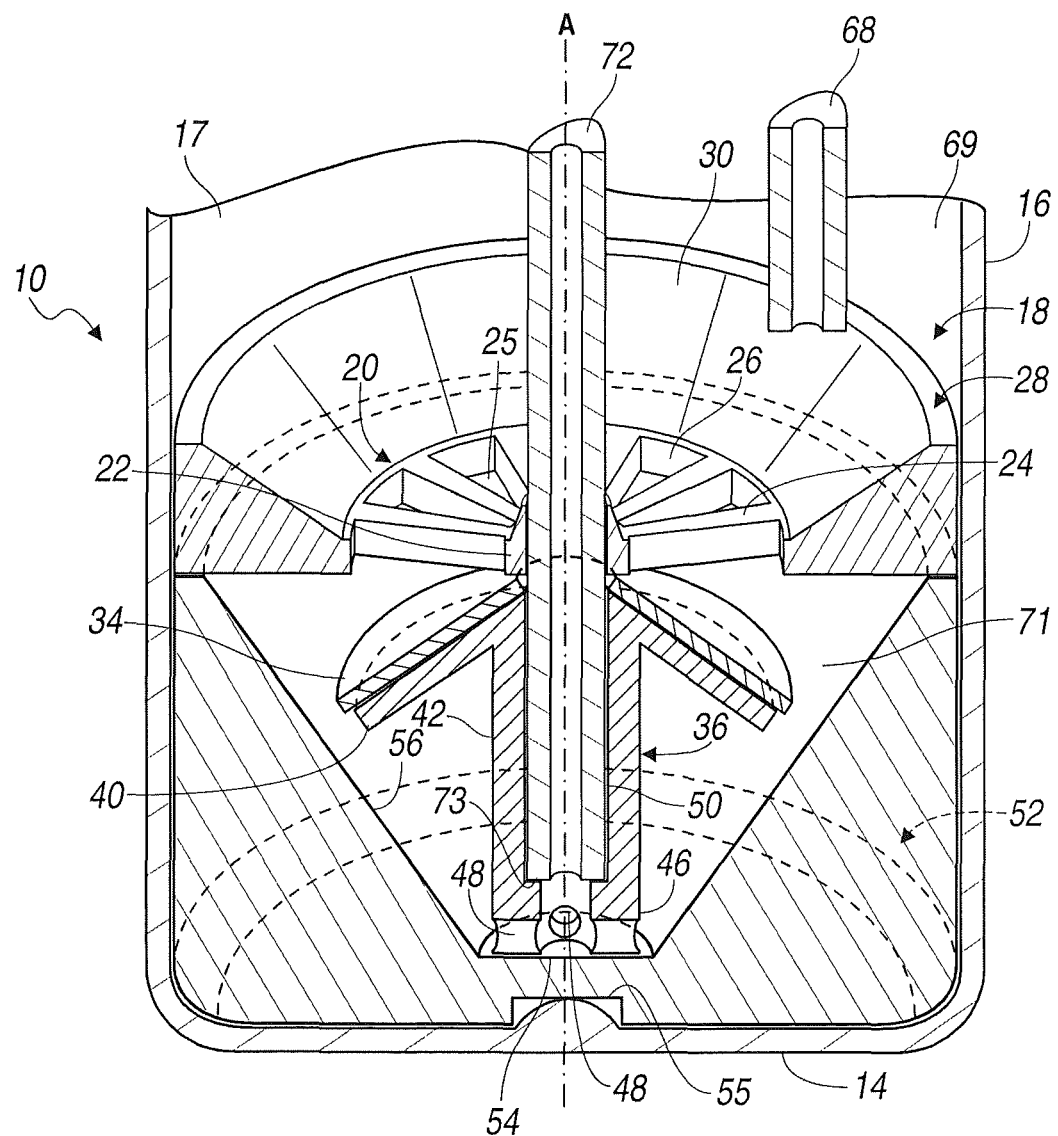
FIG. 3 is a side cross-sectional perspective view of the valve of FIG. 2 in an open position.

With initial reference to FIGS. 1-3, a separation device in accordance with the present teachings is illustrated at reference numeral 10. The separation device 10 generally includes a first end 12, a second end 14 that is opposite to the first end 12, and a sidewall 16 that extends between the first end 12 and the second end 14. The sidewall 16 defines a separation chamber 17 of the separation device 10 having an interior volume. The sidewall 16 can be cylindrical. As illustrated, the first end 12 and the second end 14 can be positioned in spaced apart, parallel planes that are perpendicular to a longitudinal axis A of the separation chamber 17. The separation chamber 17 can have an interior volume of any suitable size, such as 90 ml, with any suitable diameter, such as 1.35 inches.

Figure 4:
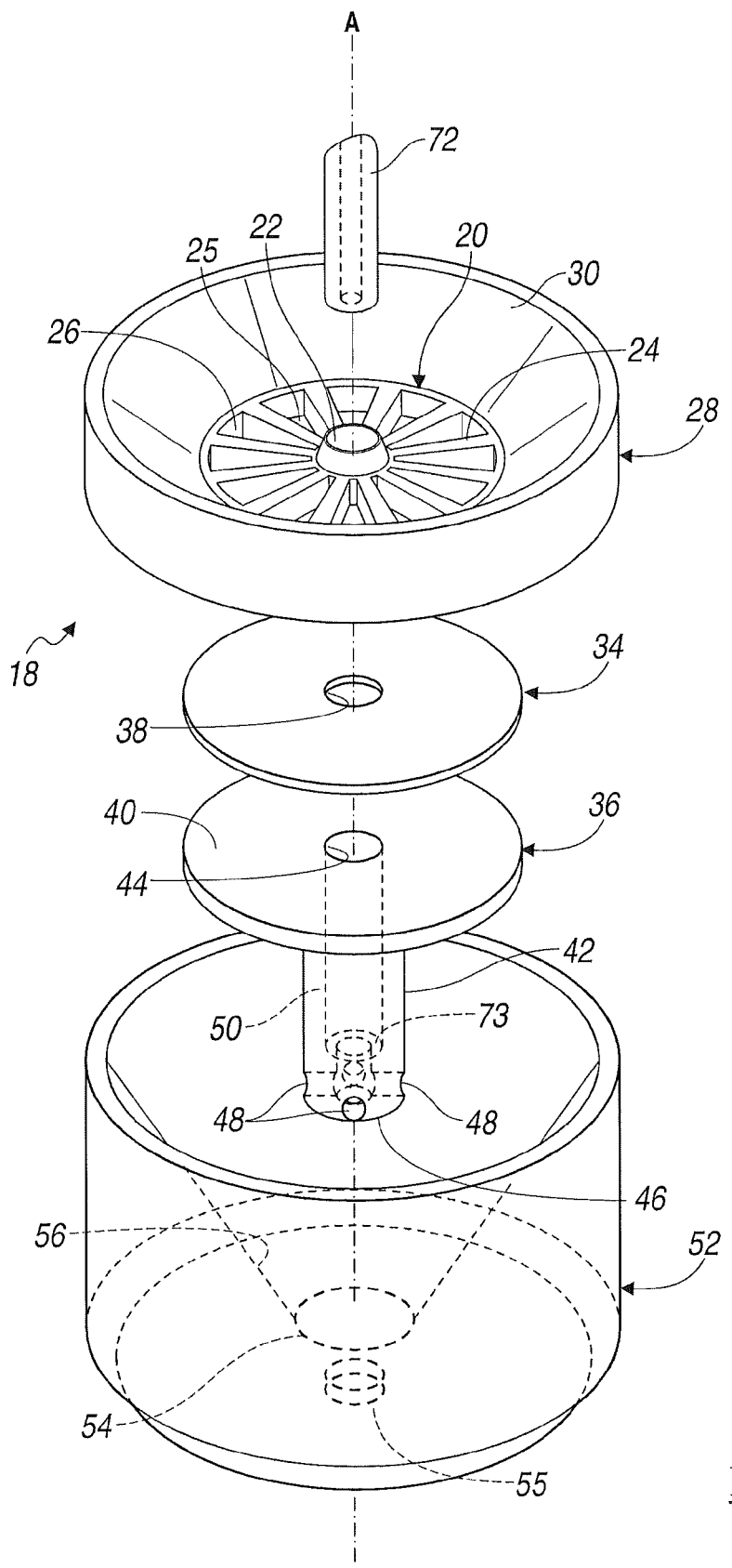
FIG. 4 is an exploded perspective view of the valve.

With additional reference to FIG. 4, a valve 18 is mounted at a fixed position within the separation chamber 17. Thus, the valve 18 does not move along the longitudinal axis A of the chamber 17. The valve 18 includes a grate or screen 20. The grate 20 is generally cylindrical and includes a center opening 22 with a series of radially extending spokes 24 extending therefrom. Each of the spokes 24 define an opening or passageway 25 therebetween. The spokes 24 terminate at a cylindrical outer wall 26. As illustrated, the passageways 25 are pie-shaped. However, the openings can be of any suitable shape, such as square or circular, as described below.

The grate 20 is surrounded by an annular insert 28 having a conical surface 30 that is angled toward the grate 20 to direct materials on the conical surface 30 toward the grate 20. The insert 28 has an outer diameter 32 that approximates an inner diameter of the separation chamber 17, such that no material can pass around the insert 28. The grate 20 and the opening 22 defined by the grate 20 provide support and alignment for a second extraction tube 72, which is further described herein. In place of the grate 20, any suitable screen with or without an opening therein can be used. Further, the grate 20 may be optional and the device 10 can be provided with the grate 20 removed and an opening provided in its place.

The valve 18 further includes a sealing member 34 and a support or valve actuation member 36. As illustrated, the sealing member 34 and the valve actuation member 36 can be aligned along the longitudinal axis A of the separation chamber 17. The sealing member 34 is generally shaped as a cylindrical disk and includes an opening 38 at its axial center. The sealing member 34 can be made of any suitable material, including a flexible material, such as a silicone rubber material. The sealing member 34 is sized to seal the plurality of passageways 25.

The valve actuation member 36 can include a cylindrical disk 40 and a mounting tube 42 extending therefrom along a longitudinal axis of the valve actuation member 36. The cylindrical disk 40 has a circumference that is substantially similar to that of the sealing member 34. The cylindrical disk 40 includes an opening 44 at its axial center. As further described herein, the cylindrical disk 40 provides support for the sealing member 34 to position the sealing member 34 against the grate 20 and prevent the passage of materials through the passageways 25 when the valve 18 is in the closed position. Further, the cylindrical disk 40 is flexible in response to gravitational forces, such as those experienced during centrifugation, to move the sealing member 34 from contact with the grate 20 and permit the passage of materials through the passageways 25 when the valve 18 is in the open position.

The mounting tube 42 extends from the cylindrical disk 40 along the axial center of the cylindrical disk. The mounting tube 42 has a circumference that is generally smaller than the circumference of the cylindrical disk 40. Proximate to a distal end 46 of the mounting tube 42 is at least one aperture 48. As illustrated, the distal end 46 includes four of the apertures 48, which are spaced evenly about the mounting tube 42 at approximately 90° intervals. A through port 50 extends between the apertures 48 and the opening 44 to provide fluid communication through the valve actuation member 36.

The cylindrical disk 40 of the valve actuation member 36 can be formed of any suitable material that can flex when a force is applied to it, such as a centrifugal force or a pressure differential force. For example, the disk 40 can be any resilient member operable to bias the valve 18 in a closed position such that the sealing member 34 blocks the passage of materials through the passageways 25. Material selected for the cylindrical disk 40 can include acrylic, polycarbonate, and any other appropriate resilient, flexible, and substantially inert material. The sealing member 34 can be mounted to the cylindrical disk 40 in any suitable manner, such as by using a suitable adhesive. Alternatively, the sealing member 34 can be a coating on the disk 40 and/or integral with the disk 40. The sealing member 34 can also be a separate component that is not secured to the disk 40, but rather sits thereon and is supported by the disk 40.

The assembled valve 18 is positioned within the separation chamber 17 such that the distal end 46 of the mounting tube 42 abuts the second end 14 of the chamber 17, which may include a funnel 52 as further described herein. The grate 20, the sealing member 34, and the valve actuating member 36, are each positioned such that the center opening 22, the opening 38, and the opening 44 respectively are all aligned along the longitudinal axis A. When the valve is in the closed position as illustrated in FIG. 2, the cylindrical disk 40 supports the sealing member 34 against the grated portion 20 of the insert 28 to block and seal the passage of materials through the passageways 25 or openings defined by the spokes 24. The insert 28 including the grate 20 can be fixedly mounted within the separation chamber 17 using any suitable fastening device, method or system. For example, the insert 28 can be mounted to an interior of the sidewall 16 using a suitable adhesive or a press fit.

With additional reference to FIG. 3, the valve 18 is illustrated in an open position. In the open position, the cylindrical disk 40 is not perpendicular to the longitudinal axis A of the separation chamber 17, as it is in the open position, but rather its perimeter is flexed downward toward the second end to space the sealing member 34 apart from the grate 20 and permit the passage of materials through the openings 25 between the spokes 24. As further described herein, movement of the cylindrical disk 40 between the closed position of FIG. 2, for example, and the open position of FIG. 3, for example, can be caused by centrifugal force or pressure exerted against the sealing member 34 and the cylindrical disk 40 when the separation chamber 17 is loaded with a multiple component composition and inserted in a centrifuge.

The funnel 52 at the second end 14 of the chamber 17 generally includes a base portion 54 at the longitudinal axis A of the separation chamber 17. Extending from the base portion 54 is an angled cylindrical sidewall 56. The sidewall 56 is angled such that it slopes from the sidewall 16 of the separation chamber 17 toward the base portion 54. Thus, the funnel 52 directs material along the angled cylindrical sidewall 56 toward the base portion 54 where the apertures 48 of the mounting tube 42 are positioned. The funnel 52 can be secured at the second end 14 in any suitable manner, such as with a suitable adhesive or a press fit. The funnel 52 can include a counterbore or recess 55 on its undersurface facing the second end 14 of the device 10. The recess 55 accommodates a dimple 57 at the second end 14 of the device 10. Cooperation between the dimple 57 and the recess 55 can retain the funnel 52 centered in the separation chamber 17. The dimple 57 can cooperate with a corresponding feature in a centrifugation device to properly position the device 10 in the centrifuge.

The separation chamber further includes a loading port 58, a first extraction port 60, and a second extraction port 62. The loading port 58 can be any suitable port that extends into the separation chamber 17 to permit the introduction of materials into the separation chamber 17. As illustrated, the loading port 58 is at the first end 12 and extends there through. The loading port 58 can also be offset from the longitudinal axis A, as illustrated. The loading port 58 can include a loading port cap 64 that can be fastened to the port 58 using any suitable connection, such as a Luer lock connection. The Luer lock connection can also cooperate with a device for delivering the multiple component material to the separation chamber 17, such a syringe.

The first extraction port 60 can be any suitable port that extends into the separation chamber 17 to permit the withdrawal of one or more components of a multiple component material from within the separation chamber 17. As illustrated, the first extraction port 60 is at the first end 12 and extends there through. The first extraction port 60 can include a cap 66 that can be fastened to the first extraction port 60 using any suitable connection, such as a Luer lock connection. The Luer lock connection can also cooperate with a device for withdrawing the components from within the separation chamber 17, such as a syringe. Extending from the first extraction port 60 can be a first extraction tube 68. As illustrated, the first extraction tube 68 extends from the port 60 to a position proximate to a first side 69 of the valve 18 that faces the first end 12. However, one skilled in the art will recognize that the extraction tube 68 can be of any suitable length to extract a desired component of the multiple component composition of a specific density. For example, if the composition includes adipose tissue and purified fat is desired for extraction, then the extraction tube 68 can extend approximately 1.5 inches from the first end 12, such as in applications where 60 ml of adipose tissue is loaded for separation in the separation chamber 17 having a diameter of about 1.35 inches and a volume of about 90 ml. This is because purified fat is typically one of the least dense fractions of adipose tissue. Alternatively, if one or more of the more dense fractions of adipose tissue is desired for extraction, such as oil or excess/tumescent fluid, then the extraction tube 68 can extend from the first end 12 to a distance that is about 0.25 inches from the valve 18. Such a longer extraction tube 68 can also be use to extract purified fat by drawing off the more dense fractions prior to drawing the purified fat.

The second extraction port 62 can be any suitable port that extends into the separation chamber 17 to permit the withdrawal of one or more components of the multiple component material from within the separation chamber 17. As illustrated, the second extraction port 62 is at the first end 12 and extends there through. The second extraction port 62 can include a cap 70 that can be fastened to the second extraction port 62 using any suitable connection, such as a Luer lock connection. The Luer lock connection can also cooperate with a device for withdrawing the components from within the separation chamber 17, such as a syringe.

Extending from the second extraction port 62 can be the second extraction tube 72. As illustrated, the second extraction tube 72 extends from the second extraction port 62 along the longitudinal axis A to the valve 18. At the valve 18, the second extraction tube 72 extends through the center opening 22 of the grate 20, through the opening 38 of the sealing member 34, through the opening 44 of the valve actuation member 36, and the through port 50 to a position proximate to the apertures 48. Thus, the second extraction tube 72 provides fluid communication between the apertures 48 and the second extraction port 62. The second extraction tube 72 can sit on a shoulder 73 of the mounting tube 42 and can be secured within the valve 18, such as within the through port 50, in any suitable manner, such as with a press-fit or a suitable adhesive.

Figure 5:
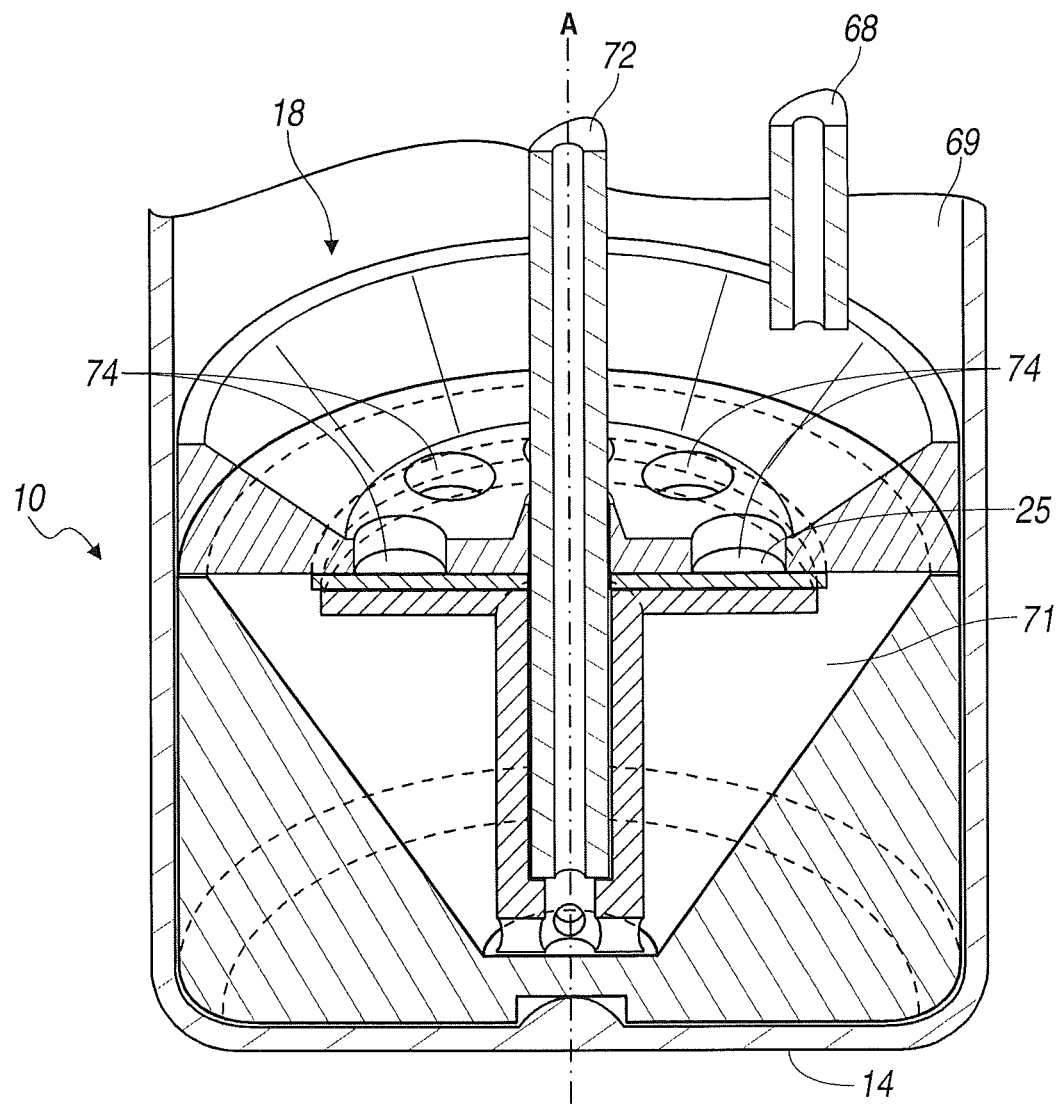
FIG. 5 is a side cross-sectional perspective view of another valve according to the present teachings.

One skilled in the art will appreciate that the grate or screen 20 can be provided in a variety of different configurations in addition to those illustrated. Accordingly and with additional reference to FIG. 5, the grate or screen 20 can include round cutouts 74 in place of the spokes 24. Any other shaped opening or cutout can also be used that will permit passage of select fractions of a multiple component material.

With additional reference to FIGS. 6-9, use of the separation device 10 to separate adipose tissue into different fractions including cellular material, purified fat, and tumescent fluid is described below. This description is for exemplary purposes only because the separation device 10 can be used to separate fractions of a wide variety of different multiple component materials.

Figure 6:
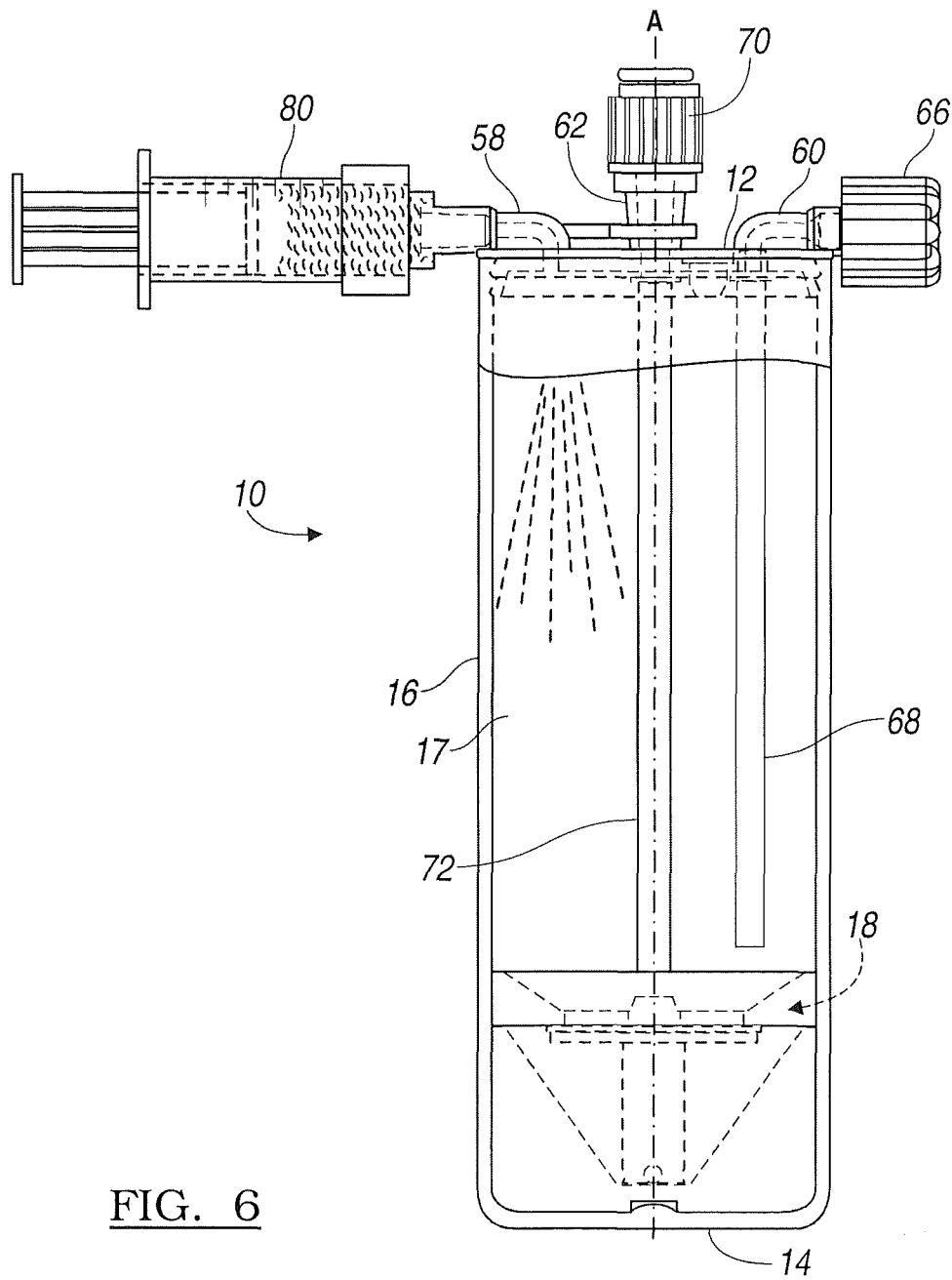
FIG. 6 is a partially cut-away side view of the separation device being filled with a multiple component material, such as adipose tissue, for separation into at least two fractions.

With initial reference to FIG. 6, the multiple component composition, such as adipose tissue, is loaded into the separation chamber 17 through the loading port 58. The adipose tissue can be delivered to the separation chamber 17 using any suitable transfer device, such as a syringe 80. The adipose tissue is loaded with the valve 18 in the closed position of FIG. 2. Thus, the adipose tissue will initially be seated atop the valve 18 on the first side 69 of the valve 18 proximate to the first end 12. Any suitable amount of adipose tissue can be used, such as about 60 ml. when a 90 ml. separation chamber having a diameter of 1.35 inches is used.

Prior to being loaded in the separation chamber 17, the adipose tissue, or any multiple component composition, can be optionally subject to mechanical disruption. Mechanical disruption loosens the adipose tissue to facilitate separation of the different fractions during further processing. Any suitable disruptor can be used, such as the disruptors described in U.S. application Ser. No. 12/395,085 titled "A System For Separating A Material," which was filed on Feb. 27, 2009 and is assigned to Biomet Biologics, LLC., which is incorporated by reference herein. This type of disruptor includes a screen or grate that the multiple component material is forced through to loosen the interaction between the different fractions.

After the adipose tissue is loaded, a suitable anticoagulant, such as citrate phosphate dextrose ("CPD"), can be added as well as through the loading port 58. Any suitable amount of CPD can be added, such as about 8.5 cc for 60 cc of adipose tissue. The separation device 10 can then be incubated at about 37° C. for about five minutes. Any suitable device or method can be used to perform the incubation, such as by placing the separation device 10 in a heat bath or wrapping the device 10 in a heat pack.

Figure 7:
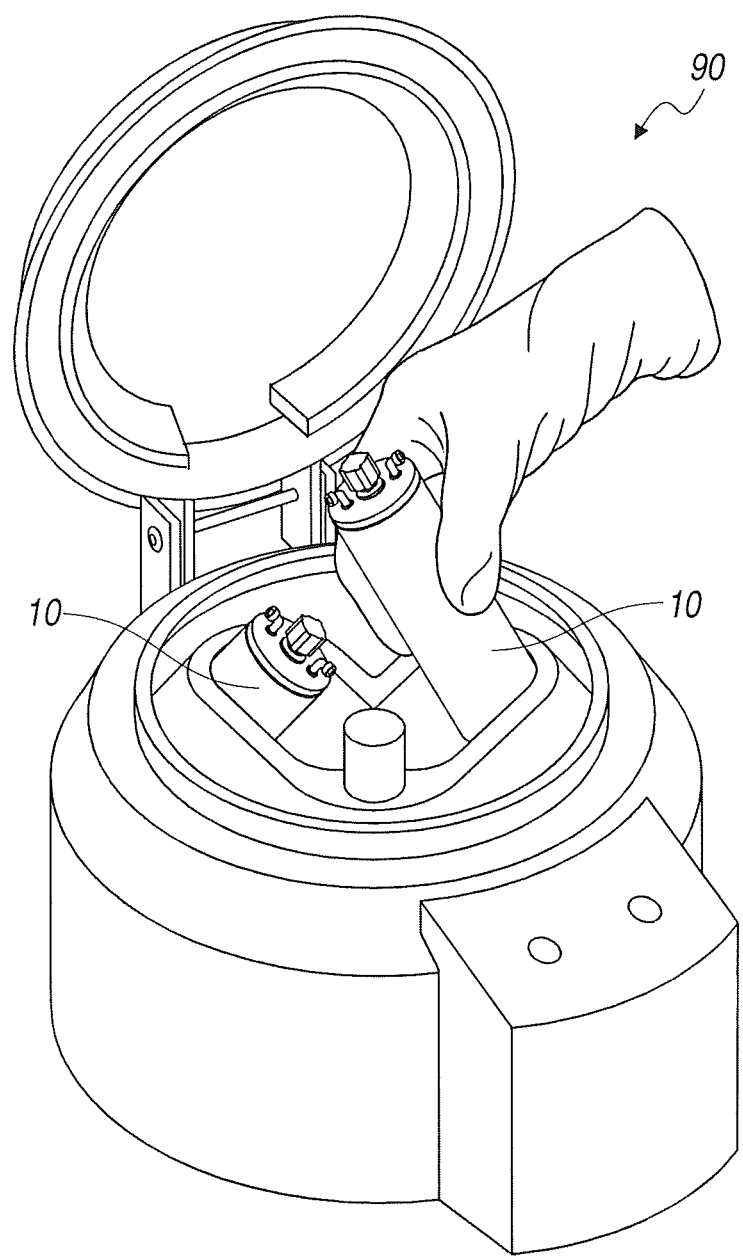
FIG. 7 is a perspective view of a centrifuge for spinning the device in order to separate the multiple component material into at least two fractions, such as cellular material and purified fat when the multiple component material is adipose tissue.
Figure 8:
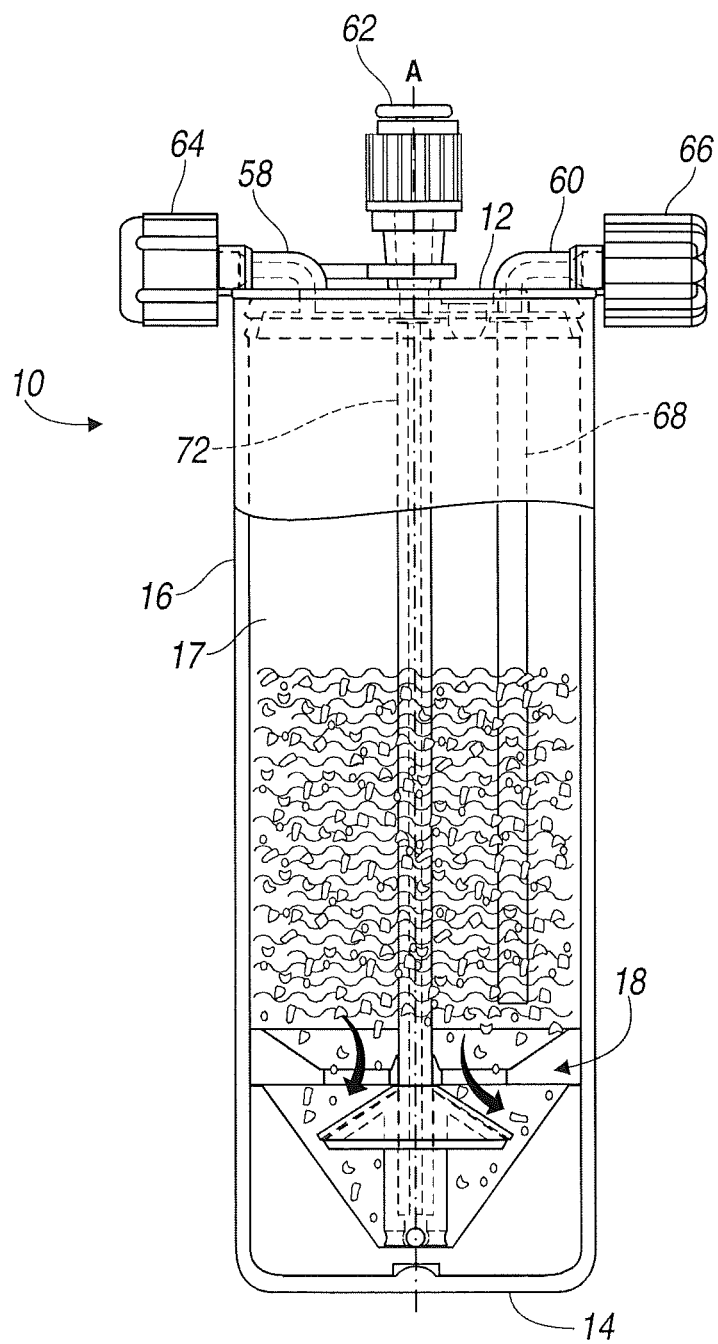
FIG. 8 is a partially cut-away side view of the separation device with the valve open, thus permitting passage of at least one fraction of the multiple component material there through, such as cellular material where the multiple component material is adipose tissue.

The separation device 10 containing the adipose tissue is then spun in a suitable rotational device, such as the centrifuge 90 illustrated in FIG. 7. As illustrated, multiple separation devices 10 can be spun simultaneously. The separation device 10 can be initially spun at about 100 to about 1,500× gravity for about 5 minutes to allow for initial separation of fat layers, including oil, fatty tissue, excess/tumescent fluid, etc. The speed of the centrifuge can then increased to about 1,500 to about 3,000× gravity for about an additional 12-15 minutes. Alternatively, the separation device 10 can be subject to a single centrifugation at about 1,500 to about 3,000× gravity and 3,200 revolutions/minute for about 15 minutes.

During centrifugation, gravitational forces act on the valve 18 to cause the valve 18 to move to the open position of FIG. 3. Specifically and with additional reference to FIG. 8, gravitational forces cause the valve actuation member 36 and the sealing member 34 mounted thereto to bend downward along the longitudinal axis A such that the outer diameter of both the valve actuation member 36 and the sealing member 34 move toward the second end 14. The valve actuation member 36 and the sealing member 34 bend at the portions proximate to the longitudinal axis A to provide a "flap valve." This separates the sealing member 34 from the grate 20 to create a space therebetween through which components of the multiple component composition, such as cellular material where the multiple component material is adipose tissue, can pass and collect at the base portion 54 of the insert 52, which along with the angled cylindrical sidewall 56 defines a sump on a second side 71 of the valve 18.

Figure 9:
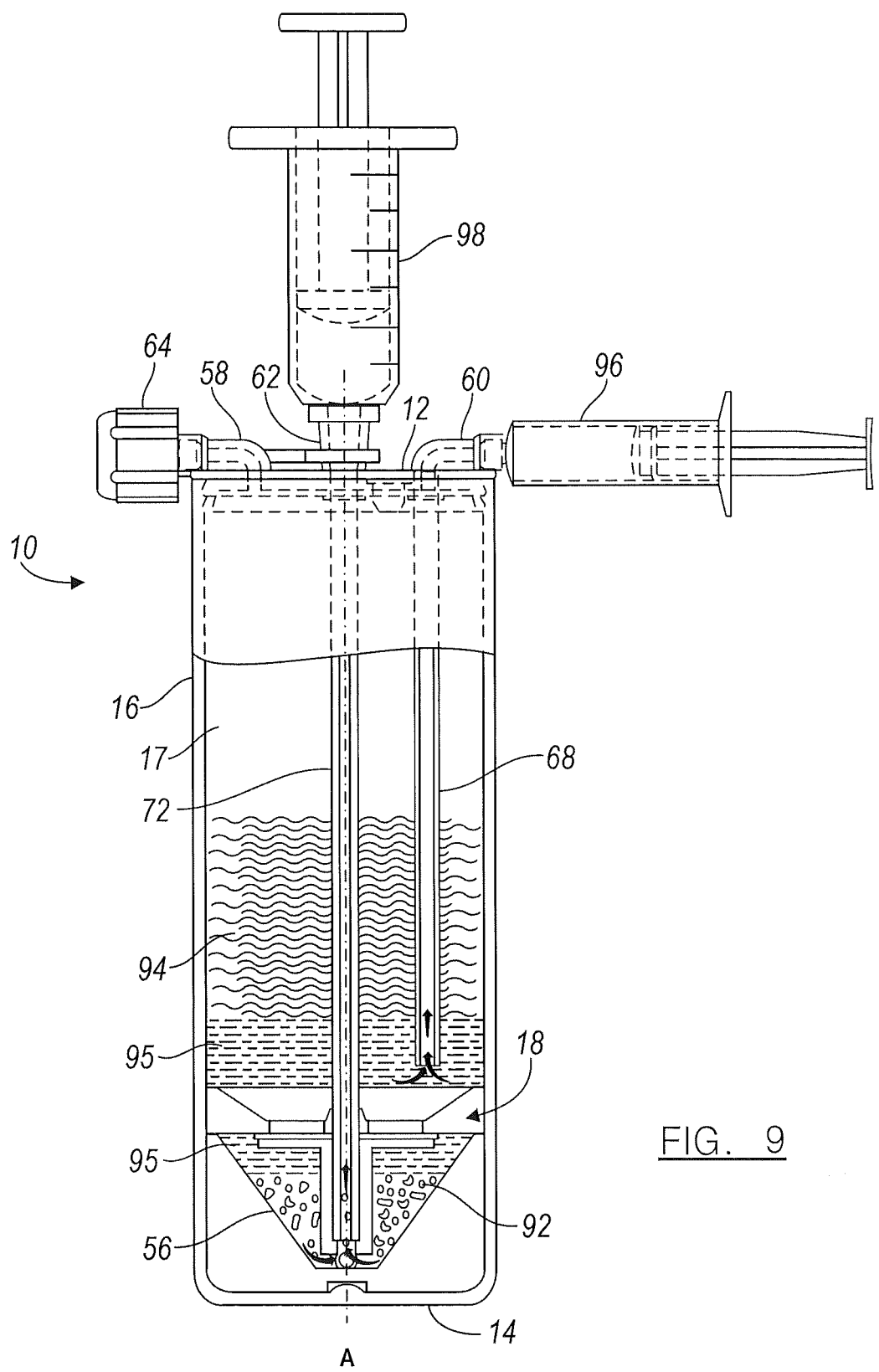
FIG. 9 is a partially cut-away side view of the separation device showing separated fractions being extracted from the separation device.

With additional reference to FIG. 9, centrifugation causes the different fractions of the multiple component material to separate according to density such that fractions with the greatest density settle at the second end 14. The least dense fractions settle proximate to the first end 12 or most distal to the second end 14. After centrifugation, the valve 18 returns to the closed position, illustrated in, for example, FIG. 9. When closed, the valve 18 separates the multiple component material such that at least one fraction of a first density is separated between the valve 18 and the second end 14, and a second fraction having a second density that is greater than the first density is separated on an opposite side of the valve 18, which is proximate to the first end 12.

The valve 18 is positioned within the separation chamber 17 along the longitudinal axis A such that after centrifugation the two fractions of the multiple component material that are most desirable are separated on opposite sides of the valve 18. One skilled in the art will recognize that the position of the valve 18 along the longitudinal axis A will depend on the densities of the most desired fractions.

For example, when the multiple component material is adipose tissue, the valve can be positioned from about 0.5 inches to about 1.5 inches, such as about 0.75 inches, from the second end 14 in applications where the separation chamber 17 has a diameter of about 1.35 inches and a volume of about 90 ml. As a result, the fractions of adipose tissue of the greatest density, including cellular material 92 having a typical density of about 1.06 g/ml to about 1.1 g/ml, will be isolated proximate to the second end 14 on the second side 71 of the valve 18. Conversely, the fractions of adipose tissue of the least density, including purified fat having a density of about 0.95 g/ml, excess water or other fluid having a density of about 1.0 g/ml, oil, etc. at 94 are isolated on the first side 69 of the valve 18. A tumescent fluid layer 95 will be isolated on both sides of the valve 18 between the cellular material 92 and the purified fat.

To provide higher cell yields, the diameter of the separation chamber 17 can be increased and/or the volume of adipose tissue can be decreased. This increases the surface area of the adipose tissue, thus making it easier for the cells to travel through the fat and extra cellular matrix (ECM) toward the second end 14.

Increased cell yields can also be provided by subjecting the fractions 94 isolated on the first side 69 of the valve 18, such as purified fat, excess fluid, oil, etc., to a second disruption and/or centrifugation process. For example, after the one or more fractions 94 are isolated through centrifugation, the fractions 94 can again be passed through the disruptor 120 to loosen the interaction between the materials and then again be centrifuged in the separation chamber 17 to permit isolation of cellular material 94 on the second side 71 of the valve 18 that was not previously isolated. Both the disruption and centrifugation processes are further described below.

With additional reference to FIG. 9, the isolated fractions can be withdrawn as desired using a suitable extraction device, such as a syringe. For example, the purified fat, excess fluid, oil, etc. 94 can be withdrawn through the first extraction port 60 using a suitable syringe 96. Similarly, the cellular material 92 can be withdrawn through the second extraction port 62, via the aperture 48 and the second extraction tube 72 using a suitable syringe 98. The angled cylindrical sidewall 56 and the base portion 54 act as a sump to direct the cellular material 92 toward the apertures 48 of the distal end 46 of the mounting tube 42 to facilitate withdrawal of the cellular material 92 through the second extraction port 62. Prior to withdrawing the purified fat through the first extraction port 60 and subsequent to withdrawing the cellular material 92 through the second extraction port 62, the tumescent fluid layer 95 can be withdrawn through the first and the second extraction ports 60 and 62.

Figure 10:
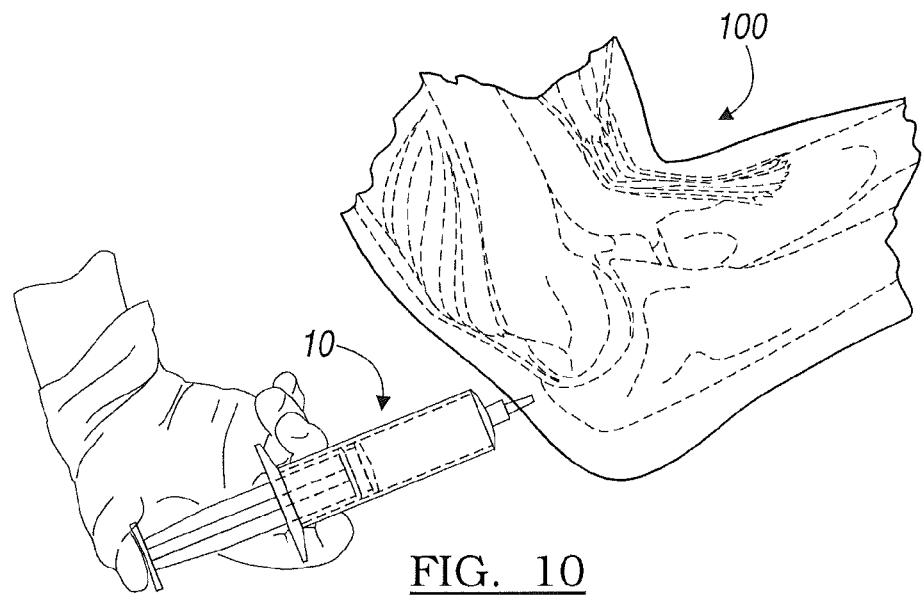
FIG. 10 illustrates delivery of one or more of the separated fractions being delivered to a selected site in a patient.

The isolated fractions can be used for a variety of different purposes. For example, the cellular material 92 can be used to facilitate wound healing, such as by directly injecting the cellular material 92 to a wound site of a patient 100, as illustrated in FIG. 10. The purified fat can be used in a variety of different types of reconstructive and cosmetic surgery, such as facial reconstruction, breast reconstruction, and in most any area in which a fat filling is desired.

Figure 11:
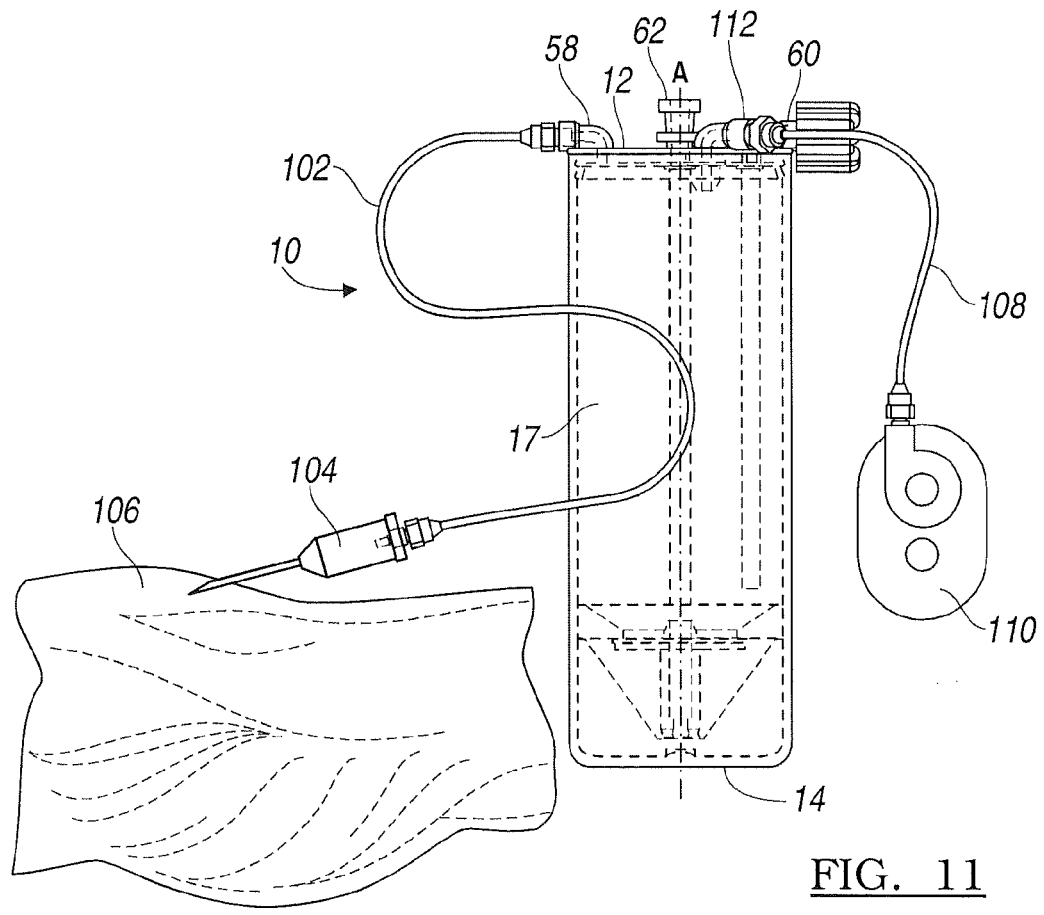
FIG. 11 illustrates extraction of the multiple component material directly from a patient into the separation device using a vacuum pump.

With additional reference to FIG. 11, a suction tube 102 with a suitable impingement device attached to an end thereof, such as a cannula 104, can be used to draw the multiple component material directly from a patient into the separation device 10. The end of the suction tube 102 opposite to the cannula 104 can be secured to the loading port 58 using any suitable connection, such as a Luer lock. The cannula 104 can be inserted directly into an area 106 of the patient from where the adipose tissue is desired to be removed.

To facilitate withdrawal of the adipose tissue from the desired area 106 of the patient, a suitable extraction device, such as a vacuum pump 110, can be used. The vacuum pump 110 can be connected to a separate vacuum port 112 at the first end 12 of the separation chamber 17 that provides fluid communication with the interior volume of the separation chamber 17. The vacuum pump 110 can be connected to the vacuum port 112 using a suitable suction tube 108. The vacuum pump 110 can be any suitable vacuum pump 110 operable to withdraw the multiple component material out of the suitable area 106 of the patient to within the separation chamber 17. After the multiple component composition is drawn into the separation chamber 17, the vacuum pump 110 can be disconnected from the vacuum port 112 and the vacuum port 112 can be closed with a suitable cap.

Figure 12:
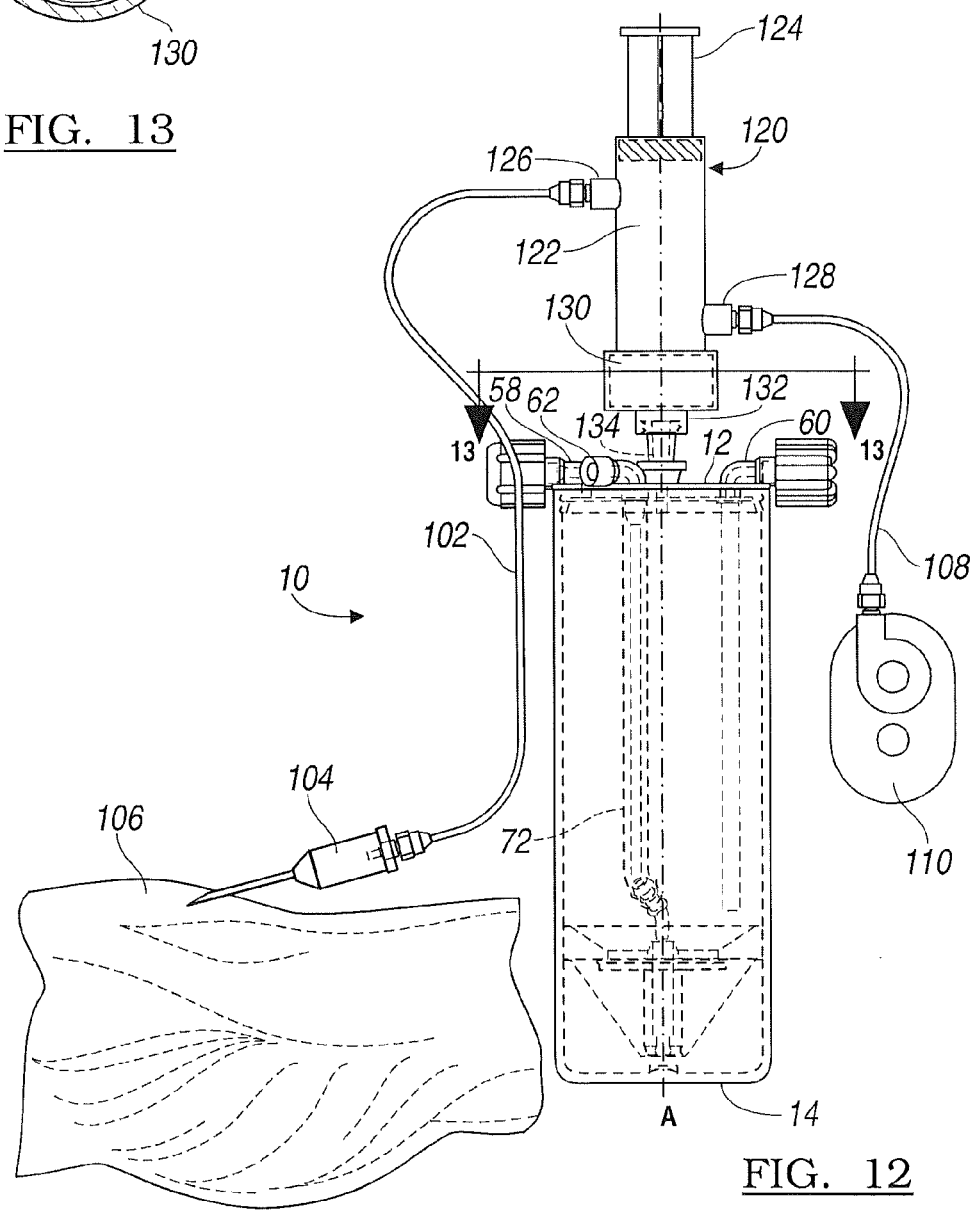
FIG. 12 is similar to FIG. 11, but includes the use of a disruption chamber attached to the separation device.

With additional reference to FIG. 12, the separation device 10 can include a suitable disruptor, such as the disruptor 120. The disruptor 120 generally includes a disruptor chamber 122, a plunger 124, a disruptor inlet port 126, a disruptor vacuum port 128, a disruption screen 130, and a disruptor outlet port 132.

The disruptor inlet port 126 provides fluid communication between an exterior of the disruptor 120 and the disruptor chamber 122. The suction tube 102 with the cannula 104 attached thereto can be connected to the disruptor inlet port 126 using any suitable connection, such as a Luer lock connection.

The disruptor vacuum port 128 also provides fluid communication between an exterior of the disruptor 120 and the disruptor chamber 122. The vacuum pump 110 can be connected to the disruptor vacuum port 128 using any suitable connection, such as a Luer lock connection, to draw the multiple component composition into the disruptor chamber 122.

Figure 13:
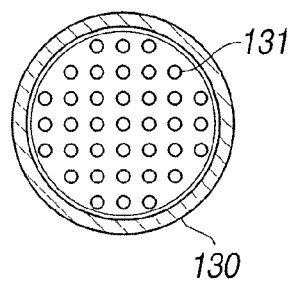
FIG. 13 is a cross-sectional view of FIG. 12 taken along line 13-13 of FIG. 12.

After a suitable amount of the multiple component material, such as adipose tissue, is drawn into the chamber 122, the pump 110 can be stopped and the plunger 124 can be depressed to drive the multiple component material through the disruption screen 130, which is also illustrated in FIG. 13. The disruption screen 130 can be any suitable disruption screen known in the art, such as those described in U.S. application Ser. No. 12/395,085 incorporated by reference herein. As illustrated, the disruption screen 130 includes a plurality of round openings 131, however any suitably shaped openings or grated surface can be provided to disrupt a material to be passed therethrough. As the material is pushed through the disruption screen, it is softened and its fractions are loosened to facilitate separation of the fractions during the centrifugation process.

The disruptor outlet port 132 is connected to an inlet port 134 of the separation device 10. As illustrated, the inlet port 134 extends through the first end 12 and is similar to the loading port 58. The inlet port 134 can be connected to the disruptor outlet port 132 in any suitable manner, such as through a Luer lock connection, to provide fluid communication between the disruptor chamber 122 and the interior volume of the separation chamber 17. Thus, as the plunger 124 is depressed, the multiple component composition is pushed through the disruptor screen 130 and into the interior volume of the separation chamber 17 where it is separated into its different fractions through centrifugation as described above. The separate inlet port 134 for the disruptor 120 is optional as the disruptor 120 can also be connected to the loading port 58.

The inlet port 134 can be located at the axial center A of the first end 12 to facilitate introduction of the adipose tissue into the separation chamber 17, however, the inlet port 134 can be located at any suitable location and can be eliminated altogether because the disruptor 120 can also be connected to the loading port 58. When the inlet port 134 is located at the axial center A, the second extraction port 62 can be moved offset from the axial center A. Accordingly, the second extraction tube 72 does not extend entirely along the axial center A as described above, but can be offset with an elbow portion 136. The inlet port 134 can be in addition to, or can take the place of, the loading port 58.

While the disruptor screen 130 is illustrated as being integral with the disruptor 120, the disruptor screen 130 can also be a separate component that is connected to both the disruptor inlet port 126 and the disruptor 120 using suitable fastening devices, such as Luer lock connections. Further, the disruptor screen 130 can be integral with the separation device 10 and the disruptor 120 can be connected to the disruptor screen 130 with a suitable connection.

While the disruptor 120 is illustrated as being connected to a single separation device 10, the disruptor 120 can be connected to multiple separation devices 10 through the use of a suitable connection device, such as a branch connector, that will provide fluid communication between the disruptor 120 and inlet ports of multiple separation chambers.

The present teachings further provide for a sterile method of using the separation device 10. With reference to FIGS. 11 and 12, the cannula 104 and the suction tube 102 can be sterilized and passed into a sterile field where the cannula 104 can be connected to a first end of the suction tube 102. A second end of the suction tube 102 can be connected to either the loading port 58 of the separation device 10 (FIG. 11) or the disruptor inlet port 126 of the disruptor 120 (FIG. 12). The separation device 10 and the disruptor 120 may be inside or outside of the sterile field depending on the procedure. The suction tube 108 is then connected to the vacuum pump 110, which is outside of the sterile field, and either the first extraction port 60 (FIG. 11) or the disruptor vacuum port 128 (FIG. 12). Thus, the separation device 10 need not ever enter the sterile field, thus allowing it to be handled by non-sterile personnel for processing in the centrifuge 90. Use of the device 10 outside of the sterile field is advantageous because it frees up space in the sterile area. Use of the device 10 inside of the sterile area decreases the possibility of contamination.

To facilitate collection of the multiple component composition, multiple cannulas 104 can be inserted into area 106 of the patient from where the composition is to be removed and multiple suction tubes 102 can be connected to the cannulas 104. The suction tubes 102 can then be connected to the loading port 58 or the disruptor inlet port 126 using a suitable connecting device, such as a suitable branch connector. Also, multiple vacuum pumps 110 can be used to increase the vacuum force. The pumps 110 can be connected to the first extraction port 60 or the disruptor vacuum port 128 using multiple suction tubes 108 connected by, for example, a branch line.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A separation system for separating a multiple component material into at least two fractions comprising:
 a separation device having a first end, a second end opposite to the first end, and a sidewall that extends between the first end and the second end to define a separation chamber having an interior volume; and
 a valve moveable between an open position and a closed position, the valve is mounted at a fixed location within the separation chamber at a position that is closer to the second end than to the first end and is spaced apart from the second end, the valve is operable to isolate a first fraction of the multiple component material having a first density on a first side of the valve from a second fraction having a second density on a second side of the valve that is opposite to the first side, wherein the valve includes a screen, a valve activation member, and a seal, each of the screen, the valve activation member, and the seal define a through hole at an axial center thereof;

wherein the through hole is in fluid communication with apertures at an end of the valve activation member proximate to the second end; and wherein an extraction tube is seated in the through hole and is connected to an extraction port of the separation device.

2. The separation system of claim 1, further comprising a sump base having angled walls at the second end of the separation device, the valve is between the first end of the separation device and the sump base.

3. The separation system of claim 1, wherein the valve includes an insert having a conical surface that extends between the sidewall and a longitudinal axis of the separation chamber, the conical surface is angled downward toward the second end of the separation chamber.

4. The separation system of claim 1, wherein the screen defines openings that are one of circular and pie-shaped.

5. The separation system of claim 1, wherein the seal that is one of the following: fastened to the activation member, integral with the activation member, and separate from the activation member.

6. The separation system of claim 5, wherein the valve activation member is movable between a closed position and an open position, in the closed position the valve activation member and the seal extend along a plane that is perpendicular to a longitudinal axis of the separation chamber and the seal contacts a grated portion of the valve to prevent the passage of material through the screen, in the open position the valve activation member and the seal are flexed toward the second end and the seal is spaced apart from the grated portion of the screen to permit the passage of material through the valve.

7. The separation system of claim 1, further comprising a disruptor and a vacuum pump in communication with the separation chamber.

8. The separation system of claim 1, wherein the multiple component material includes adipose tissue;

wherein the first fraction is isolated between the valve and the second end, the first fraction includes cellular material;

wherein the second fraction is isolated between the valve and the first end, the second fraction includes fat; and wherein a third fraction is isolated between the valve and the first fraction and between the valve and the second fraction, the third fraction includes tumescent fluid.

9. A separation system for separating a multiple component material into at least two fractions comprising:

a separation device having a first end, a second end opposite to the first end, and a sidewall that extends between the first end and the second end to define a separation chamber having an interior volume; and a valve mounted at a fixed positioned within the separation chamber at a position that is closer to the second end than to the first end and is spaced apart from the second end, the valve includes:

a screen;

a flexible valve actuation member that is movable in response to gravitational forces applied to the separation device; and a sealing member supported by the flexible valve actuation member;

wherein each of the screen, the flexible valve actuation member, and the sealing member define a through hole at an axial center thereof;

wherein the through hole is in fluid communication with apertures at an end of the valve activation member proximate to the second end; and wherein an extraction tube is seated in the through hole and is connected to an extraction port of the separation device;

wherein the flexible valve actuation member and the sealing member extend in a plane perpendicular to a longitudinal axis of the separation chamber and the sealing member contacts the screen to prevent the passage of materials through the screen when the valve is in a closed position; and wherein the flexible valve actuation member and the sealing member bend toward the second end when the valve is in an open position in response to gravitational forces exerted upon the separation device such that the sealing member is spaced apart from the screen to permit the passage of material through the screen.

10. The separation system of claim 9, wherein the valve is operable to isolate a first fraction of the multiple component material having a first density on a first side of the valve from a second fraction having a second density on a second side of the valve that is opposite to the first side, and the valve is operable to isolate a third fraction including tumescent fluid between the valve and the first fraction and between the valve and the second fraction.

11. The separation system of claim 9, further comprising a second extraction tube extending from a position that is proximate to a side of the valve facing the first end to a second extraction port of the separation chamber.

12. The separation system of claim 9, further comprising a disruptor and a vacuum pump in fluid communication with the separation chamber.

13. The separation system of claim 9, wherein, with adipose tissue present in the separation chamber, the valve moves to the open position when the device is spun to permit cellular material to pass through the valve; and wherein after the device is spun the valve moves to the closed position to isolate the cellular material between the valve and the second end, the cellular material can be withdrawn from the separation device for further use.

14. The separation system of claim 9, wherein the screen, the flexible valve, and the sealing member are aligned along a longitudinal axis of the separation chamber.

15. A method for isolating at least two fractions of a multiple component material comprising:

loading the multiple component material into a separation chamber of a separation device between a valve mounted at a fixed position in the separation chamber and a first end of the device, the first end is opposite to a second end and a sidewall extends between the first end and the second end to define the separation chamber having an interior volume;

wherein each of the screen, the flexible valve actuation member, and the sealing member define a through hole at an axial center thereof;

wherein the through hole is in fluid communication with apertures at an end of the valve activation member proximate to the second end; and wherein an extraction tube is seated in the through hole and is connected to an extraction port of the separation device;

centrifuging the separation device such that the valve moves to an open position in response to gravitational forces exerted on the device to permit a first fraction of the multiple component material of a first density to pass through the valve toward the second end;

ceasing centrifugation of the separation device to permit the valve to move to a closed position, thus isolating the first fraction of the first density between the valve and the second end and isolating a second fraction of a second density that is less dense than the first density between the valve and the first end; and withdrawing at least one of the first fraction and the second fraction from the separation chamber for use in a subsequent procedure.

16. The method of claim 15, further comprising loading adipose tissue into the separation chamber to isolate the first fraction including cellular material, the second fraction including purified fat, and a third fraction including tumescent fluid;

incubating the separation device with the adipose tissue loaded therein for about five minutes at about 37° C.; and centrifuging the device at a speed of about 3,200 revolutions/minute for about fifteen minutes.

17. The method of claim 15, further comprising extracting the multiple component material from a patient and simultaneously loading the material directly into the separation device using a vacuum pump.

18. The method of claim 15, further comprising subjecting the multiple component material to disruption prior to loading the multiple component material into the separation chamber.

* * * * *